(12) United States Patent
Pezzuto

(10) Patent No.: US 11,026,917 B2
(45) Date of Patent: *Jun. 8, 2021

(54) ANTIOXIDATIVE STRESS COMPOSITIONS, METHODS OF PREPARING AND USES THEREOF

(71) Applicant: John Michael Pezzuto, Glen Head, NY (US)

(72) Inventor: John Michael Pezzuto, Glen Head, NY (US)

( * ) Notice: Subject to any disclaimer, the term of this patent is extended or adjusted under 35 U.S.C. 154(b) by 115 days.

This patent is subject to a terminal disclaimer.

(21) Appl. No.: 16/531,264

(22) Filed: Aug. 5, 2019

(65) Prior Publication Data

US 2019/0350899 A1 Nov. 21, 2019
US 2020/0316018 A9 Oct. 8, 2020

Related U.S. Application Data

(60) Continuation of application No. 16/108,431, filed on Aug. 22, 2018, now Pat. No. 10,413,524, which is a (Continued)

(51) Int. Cl.
*A61K 31/366* (2006.01)
*A61K 45/06* (2006.01)
(Continued)

(52) U.S. Cl.
CPC .......... *A61K 31/366* (2013.01); *A23K 20/10* (2016.05); *A23K 20/179* (2016.05); *A23K 50/40* (2016.05); *A23K 50/42* (2016.05); *A61K 31/05* (2013.01); *A61K 31/12* (2013.01); *A61K 31/352* (2013.01); *A61K 45/06* (2013.01); *A61K 9/0056* (2013.01)

(58) Field of Classification Search
CPC ...... A61K 31/05; A61K 45/06; A61K 9/0056; A61K 31/12; A23K 20/10; A23K 20/179; A23K 50/40
See application file for complete search history.

(56) References Cited

U.S. PATENT DOCUMENTS

2006/0134014 A1* 6/2006 Scherl .................. A61K 31/355
424/49
2008/0317884 A1* 12/2008 Jewell ..................... A61P 31/00
424/736

(Continued)

OTHER PUBLICATIONS

Beverly, "Make your Own Dog Biscuits", Oct. 23, 2011, retrieved from https://www.themakeyourownzone.com/make-your-own-dog-biscuits on Jan. 20, 2021. (Year: 2011).*

(Continued)

*Primary Examiner* — Jianfeng Song
(74) *Attorney, Agent, or Firm* — Davidson, Davidson & Kappel, LLC

(57) ABSTRACT

Antioxidative stress compositions, methods of using antioxidative stress composition and methods of preparing antioxidative stress composition compositions are described. The antioxidative stress compositions may be chemopreventive and/or immunomodulatory. Resveratrol, genistein, ellagic acid, curcumin and quercetin may be included in the antioxidative stress composition compositions individually or in any combination.

16 Claims, 3 Drawing Sheets

Related U.S. Application Data division of application No. 15/489,914, filed on Apr. 18, 2017, now abandoned.

(60) Provisional application No. 62/340,364, filed on May 23, 2016, provisional application No. 62/391,115, filed on Apr. 20, 2016.

(51) Int. Cl.

| | |
|---|---|
| A23K 50/42 | (2016.01) |
| A23K 20/179 | (2016.01) |
| A23K 50/40 | (2016.01) |
| A61K 31/05 | (2006.01) |
| A23K 20/10 | (2016.01) |
| A61K 31/12 | (2006.01) |
| A61K 31/352 | (2006.01) |
| A61K 9/00 | (2006.01) |

(56) References Cited

U.S. PATENT DOCUMENTS

| | | | |
|---|---|---|---|
| 2009/0182036 A1* | 7/2009 | Krammer-Lukas | A23K 20/158 514/456 |
| 2010/0112136 A1* | 5/2010 | Ward | A23K 20/111 426/72 |
| 2010/0286273 A1* | 11/2010 | Fretwell | A23K 20/142 514/561 |
| 2012/0028891 A1* | 2/2012 | Paetau-Robinson | A61K 35/57 514/4.8 |

OTHER PUBLICATIONS

Adrian, J. A., Deliramich, A. N.& Frueh, B. C. Complicated grief and posttraumatic stress disorder in humans' response to the death of pets/animals. *Bul. Menninger Clin.* 73, 176-187 (2009).
Langdon, S. P. Animal modelling of cancer pathology and studying tumor response to therapy. *Curr. Drug Targets* 13, 1535-1547 (2012).
Tilley, L.P. et al. (2007) Osteosarcoma. In: Blackwell's five-minute veterinary consult: canine and feline (ed. Blackwell Publishing) 1006-1007 (Ames, 2007).
Burry, M. Managing costs of cancer treatment for dogs. PetCareRx. (2013) Available at: https://www.petcarerx.com/article/managing-costs-of-cancer-treatment-for-dogs/1232) (accessed on Feb. 4, 2016).
Sporn, M. B. & Suh, N. Chemoprevention: an essential approach to controlling cancer. Nat. Rev.Cancer 2, 537-43 (2002).
Barrett, J.C. Mechanisms of multistep carcinogenesis and carcinogen risk assessment. Environ. Health Perspect. 100, 9-20 (1993).
Kurahashi, N. at al. JPHC Study Group. Vegetable, fruit and antioxidant nutrient consumption and subsequent risk of hepatocellular carcinoma: a prospective cohort study in Japan. Br. J. Cancer. 100, 181-184 (2009).
Tantamango-Bartley, Y., Jaceldo-Siegl, K., Fan, J. & Fraser, G. Vegetarian diets and the incidence of cancer in a low-risk population. Cancer Epidemiol Biomarkers Prey. 22, 286-294 (2012).
Orlich, M.J. ct al. Vegetarian dietary patterns and the risk of colorectal cancers. JAMA Intern. Med. 175, 767-776 (2015).
Benetou,V. et al. Vegetables and fruits in relation to cancer risk: evidence from the Greek EPIC Cohort Study. Cancer Epidemiol. Biomarkers Prev. 17, 387-392 (2008).
Cohen, J.H., Kristal, A.R. & Stanford, J.L. Fruit and vegetable intakes and prostate cancer risk. JNatl. Cancer Inst. 92, 61-68 (2000).
Pezzuto, J. M. Plant-derived anticancer agents. Biochem. Pharmacol. 53, 121-133 (1997).
Gullett, N. P. et al. Cancer prevention with natural compounds. Semin. Oncol. 37, 258-281 (2010).
Surh, Y.-J. Cancer chemoprevention with dietary phytochemicals. Nat. Rev. Cancer 3, 768-780 (2003).
Cerutti, P. Prooxidant states and tumor promotion. Science 227, 375-381 (1985).
Collins, A. R. The comet assay for DNA damage and repair. Mol. Biotech. 26, 249-261 (2004).
Antonia, S.J., Larkin, J. & Ascierto, P.A. Immuno-oncology combinations: a review of clinical experience and future prospects. Clin Cancer Res. 20, 6258-6268 (2014).
Hertzog, P. et al. Systems biology of interferon responses. J. Interferon Cytokine Res. 31, 5-11 (2011).
Billiau, A. et al. Interferon-gamma: a historical perspective. Cytokine growth factor rev. 20, 97-113 (2009).
Kosmaczewska, A. Low-dose interleukin-2 therapy: a driver of an imbalance between immune tolerance and autoimmunity. Int. J. Mol. Sci. 15, 18574-18592 (2014).
Kawaratani, H. et al. The effect of inflammatory cytokines in alcoholic liver disease. Mediators of Inflammation. Hindawi Publishing Corporation, (2013).
Feng, D., Qiu, F., Tong, Z. & Xie, C. Oral pharmacokinetic comparison of different genistein tablets in Beagle dogs. J. Chromat. Science 51, 335-340 (2013).
Colitti, M., Gaspardo, D., Dellapria, A., Scaini, C. & Stefanon, B. Transcriptome modification of White blood cells after dietary administration of curcumin and non-steroidal anti-inflammatory drug in osteoarthritic affected dogs. Vet. Immunol. Immunopathol. 147, 136-146 (2012).
Lee, J. H., Shin, Y. J. , Oh, J. H. & Lee, Y. J . Pharmacokinetic interactions of clopidogrel with quercetin, telmisartan, and cyclosporine A in rats and dogs. Arch. Phann. Res. 35, 1831-1837 (2012).
Muzzio, M. et al. Detennination ofresveratrol and its sulfate and glucuronides metabolites in plasma by LC-MS and their pharmacokinetics in dogs. J. Pharm. Biomed. Anal. 59, 201-208 (2012).
Maier-Slamon, A. et al. Hepatic glucuronidation of resveratrol: interspecies comparison of enzyme kinetic profiles in human, mouse, rat, and dog. Drug Metab. Pharrnacokinet. 26, 364-373 (2011).
Johnson, W.D. et al. Subchronic oral toxicity and cardiovascular safety pharmacology studies of resveratrol, a naturally occurring polyphenol with cancer preventive activity. Food Chem. Toxicol. 49, 3319-3327 (2011).
Chen, T. et al. Randomized phase II trial of lyophilized strawberries in patients with dysplastic precancerous lesions of the esophagus. Cancer Prev. Res. 5, 41-50 (2011).
Gupta, S.C., Patchva, S. & Aggarwal, B.B. Therapeutic roles of curcumin: lessons learned from clinical trials. AAPS Journal 15, 195-218 (2013).
Russo, M. et al. The flavonoid quercetin in disease prevention and therapy: facts and fancies. Biochem. Pharmacol. 83, 6-15 (2012).
Sporn, M.B. Combination chemoprevention of cancer. Nature 287, 107-108 (1980).
Russo, M. et al. Understanding genistein in cancer: The "good" and the "bad" effects: A review. Food Chem. 196, 589-600 (2016).
Barnes, S. et al. The metabolism and analysis of isoflavones and other dietary polyphenols in foods and biological systems. Food Funct. 2, 235-244 (2011).
Patterson, S. L., Colbert Maresso, K. & Hawk, E. Cancer chemoprevention: successes and failures. Clin. Chem. 59, 94-101 (2013).
Baek, S.J., McEntee, M.F. & Legendre, A.M. Review paper: cancer chemopreventive compounds and canine cancer. Vet. Pathol. 46, 576-588 (2009).
Pezzuto, J.M. et al. The phenomenon of resveratrol: redefining the virtues of promiscuity. Ann. N .Y. Acad .Sci. 1215, 123-130 (2011).
Calamini, B.K. et al. Pleiotropic mechanisms facilitated by resveratrol and its metabolites. Biochem. J. 429, 273-282 (2010).
Park, E.-J & Pezzuto, J .M. The pharmacology of resveratrol in animals and humans. Biochim. Biophys. Acta 1852, 1071-1113 (2015).
Aggarwal, B.B. & Shishodia, S. (eds.), Resveratrol in Health and Disease, New York, New York: Marcel Dekker, Inc., pp. 679 (2006).
Zhang, H.M. et al. Research progress on the anticancer actions and mechanisms of ellagic acid. Cancer Biol. Med. 11, 92-100 (2014).

(56) References Cited

OTHER PUBLICATIONS

Priyadarsini, R.V. et al. Gene expression signature of DMBA-induced hamster buccal pouch carcinomas: modulation by chlorophyllin and ellagic acid. PLoS One 7, e34628 (2012).
Goel, A. et al. Curcumin as "Curecumin": from kitchen to clinic. Biochem. Phannacol. 75, 787-809 (2007).
Helson, L. et al. Infusion pharrnacokinetics of LipocurcTM(liposomal curcumin) and its metabolite tetrahydrocurcumin in Beagle dogs. Anticancer Res. 32, 4365-4370 (2012).
Bames, S. et al. Soy isofiavonoids and cancer prevention. Underlying biochemical and pharmacological issues. Adv. Exp. Med. Biol. 401, 87-100 (1996).
Cai, X. et al. Bioavailability of quercetin: problems and promises. Curr. Med. Chem. 20, 2572-2582 (2013).
Russo, G.L. et al. Quercetin:a pleiotropic kinase inhibitor against cancer. Cancer Treat. Res. 159, 185-205 (2014).
Webster, J.D. et al. Recommended guidelines for the conduct and evaluation of prognostic studies in veterinary oncology. Vet. Pathol. 48, 7-18 (2011).
Zhao, Y. et al. Effect of selenoprotein S on oxidative injury in human endothelial cells. J . Transl. Med. doi:10.1186/1479-5876-11-287 (2013).
Jiang, F., Zhang, Y., Dusting, G.J. & Sibley, D.R. NADPH oxidase-mediated redox signaling: roles in cellular stress response, stress tolerance, and tissue repair. Pharmacol. Rev. 63, 218-242 (2011).
Tchen, C. R. et al. Glucocorticoid regulation of mouse and human dual specificity phosphatase 1 (DUSP1) genes. J. Biol. Chem. 285, 2642-2652 (2010).
Zhou, J ., Huang, K. & Lei, X.G. Selenium and diabetes-evidence from animal studies. Free Radic. Biol. Med. 65, 1548-1556 (2013).
Dowling, A.L. & Head, E. Antioxidants in the canine model of human aging. Biochim. Biophys. Acta 1822, 685-689 (2012).
Wong, L. J . et al. Mutations in the MPV17 gene are responsible for rapidly progressive liver failure in infancy. Hepatology 46, 1218-1227 (2007).
Itoh, S. et al. Novel mechanism for regulation of extracellular SOD transcription and activity by copper: role of antioxidant-1. Free Radic. Biol. Med. 46, 95-104 (2009).
Machado, V.S. et al. Oxidative stress and inflammatory response biomarkers in dogs with mammary carcinoma. Path. Res.Practice 211, 677-68I (2015).
Woode, R.A. et al. Resveratrol decreases oxidative burst capacity and alters stimulated leukocyte cytokine production in vitro. Vet. Immunol. Immunopathol. 163, 164-73 (2015).
DeClue, A.E., Sharp, C.R., & Hannon, M. Plasma inflammatory mediator concentrattions at ICU admission in dogs with naturally developed sepsis. J Vet Med. 26, 624-630 (2012).
Errante, P. R. , Frazao, J. B. & Condino-Neto, A. The use of interferon-gamma therapy in chronic granulomatous disease. Recent Pat. Antiinfect. Drug Discov. 3, 225-230 (2008).
Condino-Neto, A. & Newburger, P. E. Interferon-gamma improves splicing efficiency of CYBB gene transcripts in an interferon-responsive variant of chronic granulomatous disease due to a splice site consensus region mutation. Blood 95, 3548-3554 (2000).
Bastien, B.C., Patil, A & Satyaraj, E. The impact of weight loss on circulating cytokines in Beagle dogs. Vet. Immunol. Immunopath. 163, 174-182 (2015).
Shanna, V. & McNeil, J. H. To scale or not to scale: the principles of dose extrapolation. Br. J. Pharmacol. 157, 907-921 (2009).
Strasser, A. et al. A simple method for the simultaneous separation of peripheral blood mononuclear and polymorphonuclear cells in the dog. Vet. Immunol. Immunopath., 62, 29-35 (1997).
Torbergsen, A.C. & Collins, A.R. Recovery of human lymphocytes from oxidative DNA damage; the apperent enhancement of DNA repair by carotenoids. Eur. J. Nutr. 39, 80-85 (2000).
Jenkinson, A. M., Collins, A. R., Duthie, S. J. , Wahle, K. W. & Duthie, G. G. The effect of increased intakes of polyunsaturated fatty acids and vitamin E on DNA damage in human lymphocytes. FASEB J. 13, 2138-2142 (1999).
Waters, J.D. et al. Noninvasive prediction of prostatic DNA damage by oxidative stress challenge of peripheral blood lymphocytes. Cancer Epidemiol. Biommarkers Prev. 16, 190&1910 (2007).
Duthie, S.J. & Dobson, V.L. Dietary flavonoids protect human colonocyte DNA from oxidative attack in vitro. Eur. J. Nutr. 38, 28-34 (1999).
Singh, N.P., McCoy, M.T. , Tice, R.R. & Schneider, E L. A simple technique for quantification of low levels of DNA damage in individual cells. Exp. Cell Res. 175, 184-191 (1988).
Tice, R.P., Andrews, P.W., Hirai, O. & Singh, N.P. The single cell gel (SCG) assay: an electrophoretic technique for the detection of DNA damage in individual cells. Adv. Exp. Med. Biol. 283, 157-164 (1991).
Azqueta, A. & Collins, A.R. The essential comet assay: a comprehensive guide to measuring DNA damage and repair. Arch. Toxicol. 87, 949-968 (2013).
Duthie, S.J., Collins, A.R., Duthie, G.G. & Dobson, V.L. The effect of increased intakes of polyunsaturated fatty acids and vitamin E on DNA damage in human lymphocytes. Mutat. Res. 393, 223-231 ( 1997).
Chomczynski, P. & Sacchi, N. Single-step method of Rna isolation by acid guanidinium thiocyanate-phenol-chloroform extraction. Anal. Biochem. 162, 156-159 (1987).
Livak, K.J. & Schmittgen, T.D. Analysis of relative gene expression data using real-time quantitative PCR and the 2(-Delta Delta C(T)) method. Methods 25, 402-408 (2001).
Park, E.-J. et al. Induction of retinoid X receptor activity and consequent upregulation of p21WAF1/CIP1 by indenoisoquinolines in MCF7 cells. Cancer Prev. Res. 4, 1-16 (2011).
Resvantage Canine obtained from https://www.onlynaturalpet.com/products/Resvantage-Resveratrol/406000.aspx (Nov. 14, 2017).
"Pill could make your dog live longer" , http://www.cnn.com/2016/10/06/health/rapamycin-dog-live-longer/index.html (Oct. 10, 2016).
"Supplement Shown to Extend Life in Animal Studies", resvantagecanine.com/html/... SupplementShownToExtendLifeInAnimals.pdf (May 17, 2008).
Woodie et al., "Resveratrol decreases oxidative burst capacity and alters stimulated leukocyte cytokine production in vitro", Veterinary Immunology and Immunopathology, vol. 163, Issues 3-4, pp. 164-173 (Feb. 15, 2015).
Kondratyuk et al., "Evidence supporting the conceptual framework of cancer chemoprevention in canines", Scientific Reports, 6:26500; www.nature.;com, (May 24, 2016).
Ettmayer et al. "Lessons learned from Market and investigational Prodrugs," Journal of Medicinal of Chemistry, 2004, vol. 47, 2394. (Year: 2004).
Vining, "Functions of Secondary Metabolites", Annu. Rev. Microbial. Oct. 1990, vol. 44, p. 406. (Year: 1990).
Mighty, "Family Dog Formula", retrieved from https://web.archive.org/web/20150113033152/https://rnightyrnix.co.nz/Dog+Nutrition+products/Farnily+Dog.htrnl, Jan. 13, 2015 (Year: 2015).
Rosenblat et al., "Monocyte-macrophage membrane possesses free radicals scavenging activity: stimulation by polyphenols or by paraoxonase 1 (PON)", Free Radical Research, 47:4, 257-267 (2013).
Vrolijk et al., "The shifting perception of antioxidants: the case of vitamin E and β-carotene", Redox Biology 4; 272-278 (2015).
Bast et al., "Ten misconceptions about antioxidants, Trends in Pharmacological sciences", vol. 34, No. 8, pp. 430-436 (Aug. 2013).
Knight, Review: Free Radicals, Antioxidants, and the Immune System, Annals of Clinical & Laboratory Science, vol. 30, No. 2. (2000).
Krishna P.L. Bhat and John M. Pezzuto "Cancer Chemopreventive Activity of Resveratrol" Program for Collaborative Research in the Pharmaceutical Sciences,Department of Medicinal Chemistry and Pharmacognosy, College of Pharmacy, and University of Illinois Cancer Center, University of Illinois at Chicago, Chicago, Illinois 60612, USA; 210-229 (2002).

\* cited by examiner

ANTIOXIDATIVE STRESS COMPOSITIONS, METHODS OF PREPARING AND USES THEREOF

This application is a continuation of U.S. Ser. No. 16/108,431, filed on Aug. 22, 2019, which is a continuation of U.S. Ser. No. 15/489,914, filed on Apr. 18, 2017, which claims the benefit of U.S. Provisional Application No. 62/391,115, filed on Apr. 20, 2016, and U.S. Provisional Application No. 62/340,364, filed on May 23, 2016, both all hereby incorporated by reference.

BACKGROUND OF THE INVENTION

Oxidation is a chemical reaction that can produce free radicals and can cause oxidative stress. Mammals, including humans and their companion animals, are adversely affected by the oxidative stress. The oxidative stress is therefore thought to be a source or a contributing factor of many disorders, including, e.g., aging, cancer, autoimmune disorders, heart disease, inflammatory disorders, bone disorders, bladder function disorders, joint health disorders, arthritis, vision, depression, anxiety, Alzheimer's disease, Parkinson's disease, dementias, diabetes, coronary artery disease, kidney disease, and viral or bacterial infections.

In addition, since the average lifespan of a healthy non-human mammal (e.g., a canine) is shorter than the average lifespan of a healthy human being, people commonly experience the loss of their companion animals[1]. More than half of dogs over 10 years of age are likely to develop cancer[2]. Although treatment measures are available for canine neoplasia, these treatment measures are typically expensive and are not very effective. For example, once diagnosed with osteosarcoma, the median survival time without treatment, with amputation alone, or with palliative radiotherapy alone, is 4 months. With surgery and chemotherapy this is increased to only 10 months[3]. In addition, while human therapies are often highly subsidized, the cost of treating service animals and pets generally falls wholly on the owners. The expense associated with treatment options varies, but may range from $6,000-10,000 for chemotherapy, $5,000-7,000 for radiation, and $2,500-6,000 for surgery[4]. Medical expenses of this magnitude are likely to pose undue hardship on millions of people nationwide.

Antioxidative stress compositions may therefore be of value in enhancing the health of mammals, including humans and non-human mammals (e.g., canines). The results reported below show significant promise and support the notion of providing and perfecting the antioxidative stress compositions, including chemopreventive compositions and immunomodulatory compositions.

SUMMARY OF THE INVENTION

The invention is directed in part to antioxidative stress compositions. The antioxidative stress compositions are bioavailable and, after oral administration, cross enterocytes and enter systemic blood circulation of mammals (e.g., canines). The antioxidative stress compositions are useful in the treatment of disorders caused by or accompanied by oxidative stress and/or inflammation. The antioxidative stress compositions may be administered, e.g., as an animal feed, as part of an animal feed, as a biscuit, as a drug for use in humans or animals, or as a dietary or nutritional supplement.

The antioxidative stress compositions comprise at least three active agents selected from the group consisting of resveratrol, genistein, ellagic acid, curcumin, quercetin, prodrugs, metabolites, salts of any of the foregoing, and mixtures of any of the foregoing. Resveratrol may comprise from about 1% to about 80% of the composition by weight, ellagic acid may comprise from about 0.25% to about 20% of the compositions by weight, genistein may comprise from about 0.5% to about 40% of the compositions by weight, curcumin may comprise from about 1% to about 80% of the compositions by weight; and quercetin may comprise from about 1% to about 80% of the compositions by weight.

The active agents in the antioxidative stress compositions generally do not adversely affect or block antioxidative properties of each other. The active agents work together to provide therapeutic effects (e.g., inhibit $H_2O_2$-induced DNA strand breakage).

The antioxidative stress compositions are formulated such that the antioxidative stress compositions after oral or intravenous administrations to mammals provide: (i) an increase in the production of IL-10 in the mammals and/or (ii) a decrease in production of IL-2 in the mammals and/or (iii) a decrease in production of IFN-γ in the mammals and/or (iv) an increase in a number of monocytes and macrophages in the mammals and/or (v) an increase in expression of CYBB, DUS, GSR, UCP2, and VIMP genes in the mammals and/or (vi) a downregulation of ATOX1, CCL5, EPX, MPV17, PRNP and SOD3 genes in the mammals and/or (vi) a reduction of oxidative stress in the mammals. In certain embodiments, the antioxidative stress compositions are formulated such that the antioxidative stress compositions after oral and intravenous administrations to mammals provide: (i) a mean serum level of resveratrol of from about 3.86 ng/ml to about 154 µg/ml and/or (ii) a mean serum level of resveratrol-3-O-glucuronide of from about 12.9 ng/ml to about 514 µg/ml and/or (iii) a mean serum level of trans-resveratrol-4'-sulfate of from about 8.9 ng/ml to about 355 µg/ml and/or (iv) a mean serum level of trans-Resveratrol-3-sulfate of from about 84.9 ng/ml to about 3397 µg/ml and/or (v) a mean serum level of cis-resveratrol-3-sulfate of from about 2.7 ng/ml to about 108 µg/ml and/or (vi) a mean serum level of resveratrol sulfate total of from about 36.7 ng/ml to about 1467 µg/ml and/or (vii) a mean serum level of genistein-4'-glucuronide of from about 14 µg/ml to about 14167 µg/ml and/or (viii) a mean serum level of genistein-4'-glucuronide of from about 1.7 µg/ml to about 1700 µg/ml and/or (ix) a mean serum level of genistein sulfate of from about 54 µg/ml to about 53836 µg/ml and/or (x) a mean serum level of curcumin glucuronide of from about 6.25 ng/ml to about 250 µg/ml and/or (xi) a mean serum level of quercetin of from about 0.2 ng/ml to about 8000 µg/ml. In certain embodiments, the antioxidative stress compositions are formulated such that the active agents in the antioxidative stress compositions provide an additive effect(s) or a synergistic effect(s).

It is believed that the prior art does not teach or suggest compositions comprising at least three active agents selected from the group consisting of resveratrol, genistein, ellagic acid, curcumin, quercetin, prodrugs, metabolites, salts of any of the foregoing, and mixtures of any of the foregoing as disclosed herein, and, therefore, the therapeutic effects of resveratrol, genistein, ellagic acid, curcumin, quercetin, prodrugs, metabolites, salts of any of the foregoing in a composition comprising at least three active agents selected from the group consisting of resveratrol, genistein, ellagic acid, curcumin, quercetin, prodrugs, metabolites, salts of any of the foregoing, and mixtures of any of the foregoing as disclosed herein are not predictable from the prior art. It is further believed that the in-vivo performance of a composition comprising resveratrol, ellagic acid, curcumin, genistein and quercetin, and its therapeutic effects, are also not predictable form the prior art.

In certain embodiments, an antioxidative stress composition comprises a therapeutically effective amount of a combination comprising at least three active agents selected from the group consisting of resveratrol, genistein, ellagic acid, curcumin, quercetin, prodrugs, metabolites, salts, and mixtures of any of the foregoing sufficient to protect DNA from oxidative stress damage in a mammal (e.g., a canine) in need thereof, and may be used to treat cancer, autoimmune disorders, heart disease, inflammatory disorders, bone disorders, bladder function disorders, joint health disorders, arthritis, vision, depression, anxiety, Alzheimer's disease, Parkinson's disease, dementias, diabetes, coronary artery disease, kidney disease, and viral or bacterial infections; or prolong longevity and/or healthspan of the mammal. The therapeutically effective amount of the combination may, e.g., be from about 0.25 mg to 8000 mg. In certain embodiments, the therapeutically effective amount is from about 0.5 mg to about 7000 mg, from about 0.75 mg to about 6000 mg, from about 1 mg to about 5000 mg, from about 2 mg to about 5000 mg, from about 3 mg to about 5000 mg, from about 4 mg to about 5000 mg; from about 5 mg to about 5000 mg, from about 6 mg to about 5000 mg, from about 7 mg to about 5000 mg, from about 8 mg to about 5000 mg, from about 9 mg to about 5000 mg, from about 10 mg to about 5000 mg, from about 12 mg to about 5000 mg, from about 14 mg to about 5000 mg, from about 16 mg to about 5000 mg, from about 18 mg to about 5000 mg, from about 20 mg to about 5000 mg, from about 25 mg to about 5000 mg; from about 30 mg to about 5000 mg, from about 40 mg to about 5000 mg, from about 40 mg to about 5000 mg, from about 50 mg to about 5000 mg, or from about 100 mg to about 5000 mg. In certain embodiments, the therapeutically effective amount of the combination may, e.g., be from about 300 mg to about 8000 mg, from about 400 mg to about 7000 mg, from about 500 mg to about 6000 mg, from about 750 mg to about 5000 mg, from about 1000 mg to about 5000 mg, from about 1500 mg to about 5000 mg. Resveratrol may comprise from about 1% to about 80% of the therapeutically effective amount by weight, ellagic acid may comprise from about 0.25% to about 20% of the therapeutically effective amount by weight, genistein may comprise from about 0.5% to about 40% of the therapeutically effective amount by weight, curcumin may comprise from about 1% to about 80% of the therapeutically effective amount by weight; and quercetin may comprise from about 1% to about 80% of the therapeutically effective amount by weight.

In certain embodiments, an antioxidative stress composition comprises a therapeutically effective amount of a combination comprising at least three active agents selected from the group consisting of resveratrol, genistein, ellagic acid, curcumin, quercetin, prodrugs, metabolites, salts, and mixtures of any of the foregoing sufficient to increase a number of monocytes and macrophages in a mammal in need thereof. Monocytes and macrophages are the first cell types responding to neoplastic stimulus. The antioxidative stress composition may therefore be used as a chemopreventive composition in the treatment or prevention of cancer in mammals.

In certain embodiments, an antioxidative stress composition comprises a therapeutically effective amount of a combination comprising at least three active agents selected from the group consisting of resveratrol, genistein, ellagic acid, curcumin, quercetin, prodrugs, metabolites, salts, and mixtures of any of the foregoing sufficient to increase expression of CYBB, DUS, GSR, UCP2, and VIMP genes; and downregulate ATOX1, CCL5, EPX, MPV17, PRNP and SOD3 genes in a mammal.

In certain embodiments, an antioxidative stress composition comprises a therapeutically effective amount of a combination comprising at least three active agents selected from the group consisting of resveratrol, genistein, ellagic acid, curcumin, quercetin, prodrugs, metabolites, salts, and mixtures of any of the foregoing sufficient to increase production of IL-10, an inflammatory cytokine that decrease the production of pro-inflammatory cytokines (e.g., TNF-$\alpha$, IL-1$\beta$, and IL-6), in a mammal. The antioxidative stress composition may therefore be used to decrease inflammation, e.g., in the treatment of cancer, autoimmune disorders, heart disease, inflammatory disorders, bone disorders, bladder function disorders, joint health disorders, arthritis, vision, depression, anxiety, Alzheimer's disease, Parkinson's disease, dementias, diabetes, coronary artery disease, kidney disease, and viral or bacterial infections.

In certain embodiments, an antioxidative stress composition comprises a therapeutically effective amount of a combination comprising at least three active agents selected from the group consisting of resveratrol, genistein, ellagic acid, curcumin, quercetin, prodrugs, metabolites, salts, and mixtures of any of the foregoing sufficient to decrease production of IFN-$\gamma$ in a mammal. IFN-$\gamma$ regulates a number of genes related to inflammation and oxidative stress. The antioxidative stress composition may therefore be used to treat conditions associated with inflammation and oxidative stress (e.g., cancer, autoimmune disorders, heart disease, inflammatory disorders, bone disorders, joint health disorders, arthritis, vision, Alzheimer's disease, Parkinson's disease, dementias, diabetes, coronary artery disease, kidney disease, and viral or bacterial infections, etc.).

In certain embodiments, an antioxidative stress composition comprises a therapeutically effective amount of a combination comprising at least three active agents selected from the group consisting of resveratrol, genistein, ellagic acid, curcumin, quercetin, prodrugs, metabolites, salts, and mixtures of any of the foregoing sufficient to decrease production of IL-2.

In certain embodiments, an antioxidative stress composition comprises a therapeutically effective amount of a combination comprising resveratrol and at least two active agents selected from the group consisting of genistein, ellagic acid, curcumin, quercetin, prodrugs, metabolites, salts, and mixtures of any of the foregoing sufficient to provide a mean serum level of resveratrol of from about 3.86 ng/ml to about 154 µg/ml, based on oral administration to a group of eight mammals.

In certain embodiments, an antioxidative stress composition comprises a therapeutically effective amount of a combination comprising resveratrol and at least two active agents selected from the group consisting of genistein, ellagic acid, curcumin, quercetin, prodrugs, metabolites, salts, and mixtures of any of the foregoing sufficient to provide a mean serum level of resveratrol-3-O-glucuronide of from about 12.9 ng/ml to about 514 µg/ml, based on oral administration to a group of eight mammals.

In certain embodiments, an antioxidative stress composition comprises a therapeutically effective amount of a combination comprising resveratrol and at least two active agents selected from the group consisting of resveratrol, genistein, ellagic acid, curcumin, quercetin, prodrugs, metabolites, salts, and mixtures of any of the foregoing sufficient to provide a mean serum level of trans-resveratrol- 4'-sulfate of from about 8.9 ng/ml to about 355 µg/ml, based on oral administration to a group of eight mammals.

In certain embodiments, an antioxidative stress composition comprises a therapeutically effective amount of a combination comprising resveratrol and at least two active agents selected from the group consisting of genistein, ellagic acid, curcumin, quercetin, prodrugs, metabolites, salts, and mixtures of any of the foregoing sufficient to provide a mean serum level of trans-resveratrol-3-sulfate of from about 84.9 ng/ml to about 3397 µg/ml, based on oral administration to a group of eight mammals.

In certain embodiments, an antioxidative stress composition comprises a therapeutically effective amount of a combination comprising resveratrol and at least two active agents selected from the group consisting of genistein, ellagic acid, curcumin, quercetin, prodrugs, metabolites, salts, and mixtures of any of the foregoing sufficient to provide a mean serum level of cis-Resveratrol-3-sulfate of from about 2.7 ng/ml to about 108 µg/ml, based on oral administration to a group of eight mammals.

In certain embodiments, an antioxidative stress composition comprises a therapeutically effective amount of a combination comprising resveratrol and at least two active agents selected from the group consisting of resveratrol, genistein, ellagic acid, curcumin, quercetin, prodrugs, metabolites, salts, and mixtures of any of the foregoing sufficient to provide a mean serum level of resveratrol sulfate total of from about 36.7 ng/ml to about 1467 µg/ml, based on oral administration to a group of eight mammals.

In certain embodiments, an antioxidative stress composition comprises a therapeutically effective amount of a combination comprising genistein at least two active agents selected from the group consisting of resveratrol, ellagic acid, curcumin, quercetin, prodrugs, metabolites, salts, and mixtures of any of the foregoing sufficient to provide a mean serum level of genistein-4'-glucuronide of from about 14 µg/ml to about 14167 µg/ml, based on oral administration to a group of eight mammals.

In certain embodiments, an antioxidative stress composition comprises a therapeutically effective amount of a combination comprising genistein and at least two active agents selected from the group consisting of resveratrol, ellagic acid, curcumin, quercetin, prodrugs, metabolites, salts, and mixtures of any of the foregoing sufficient to provide a mean serum level of genistein-4'-glucuronide of from about 1.7 µg/ml to about 1700 µg/ml, based on oral administration to a group of eight mammals.

In certain embodiments, an antioxidative stress composition comprises a therapeutically effective amount of a combination comprising genistein and at least two active agents selected from the group consisting of resveratrol, ellagic acid, curcumin, quercetin, prodrugs, metabolites, salts, and mixtures of any of the foregoing sufficient to provide a mean serum level of genistein sulfate of from about 54 µg/ml to about 53836 µg/ml, based on oral administration to a group of eight mammals.

In certain embodiments, an antioxidative stress composition comprises a therapeutically effective amount of a combination comprising curcumin and at least two active agents selected from the group consisting of resveratrol, genistein, ellagic acid, quercetin, prodrugs, metabolites, salts, and mixtures of any of the foregoing sufficient to provide a mean serum level of curcumin glucuronide of from about 6.25 ng/ml to about 250 µg/ml, based on oral administration to a group of eight mammals.

In certain embodiments, an antioxidative stress composition comprises a therapeutically effective amount of a combination comprising quercetin and at least two active agents selected from the group consisting of resveratrol, genistein, ellagic acid, curcumin, prodrugs, metabolites, salts, and mixtures of any of the foregoing sufficient to provide a mean serum level of quercetin of from about 0.2 ng/ml to about 8000 µg/, based on oral administration to a group of eight mammals.

In certain embodiments, an antioxidative stress composition comprises a therapeutically effective amount of a combination comprising resveratrol, genistein, curcumin, and quercetin sufficient to provide (i) a mean serum level of resveratrol of from about 3.86 ng/ml to about 154 µg/ml; (ii) a mean serum level of resveratrol-3-O-glucuronide of from about 12.9 ng/ml to about 514 µg/ml; (iii) a mean serum level of trans-resveratrol-4'-sulfate of from about 8.9 ng/ml to about 355 µg/ml; (iv) a mean serum level of trans-Resveratrol-3-sulfate of from about 84.9 ng/ml to about 3397 µg/ml; (v) a mean serum level of cis-resveratrol-3-sulfate of from about 2.7 ng/ml to about 108 µg/ml; (vi) a mean serum level of resveratrol sulfate total of from about 36.7 ng/ml to about 1467 µg/ml; (vii) a mean serum level of genistein-4'-glucuronide of from about 14 µg/ml to about 14167 µg/ml; (viii) a mean serum level of genistein-4'-glucuronide of from about 1.7 µg/ml to about 1700 µg/ml; (ix) a mean serum level of genistein sulfate of from about 54 µg/ml to about 53836 µg/ml; (x) a mean serum level of curcumin glucuronide of from about 6.25 ng/ml to about 250 µg/ml; and (xi) a mean serum level of quercetin of from about 0.2 ng/ml to about 8000 µg/ml, based on oral administration to a group of eight mammals.

Administration of the antioxidative stress compositions of the invention (e.g., oral administration) to a mammal in need thereof preferably results in a reduction of oxidative stress in the mammal.

The antioxidative stress compositions may be administered orally or intravenously once a day, twice a day or three times a day for a time period sufficient to provide a therapeutic effect (e.g., to reduce an antioxidative stress, or alleviate or reduce symptoms associated with the diseases caused by or accompanied by the oxidative stress). In certain embodiments, the time period sufficient to provide a therapeutic effect is from 2 weeks to 20 years. In certain embodiments, the time period is from 2 weeks to 15 years, from 2 weeks to 12 years, from 2 weeks to 10 years, from 2 weeks to 8 years, from 2 weeks to 7 years, from 2 weeks to 6 years, from 2 weeks to 5 years, from 3 weeks to 5 years, from 3 weeks to 4 years, from 4 weeks to 3 years, or from 3 weeks to 52 weeks.

Because oxidative stress causes damage to DNA, RNA, proteins, and other cellular components, the antioxidative stress compositions of the present invention may be used, e.g., to prevent, delay the onset, prophylaxis of or in treatment of cancer, autoimmune disorders, heart disease, inflammatory disorders, bone disorders, bladder function disorders, joint health disorders, arthritis, vision, depression, anxiety, Alzheimer's disease, Parkinson's disease, dementias, diabetes, coronary artery disease, kidney disease, viral or bacterial infections, and other disorders associated with, caused by or accompanied by oxidative stress. The antioxidative stress compositions may also be used to enhance vibrancy or youthfulness or appearance of a mammal and/or improve energy in a mammal. In addition, the antioxidative stress compositions may be used to prolong longevity and/or healthspan of mammals (e.g., canines). The antioxidative stress compositions may also be used in combination with conventional chemotherapeutic agents, to reduce or minimize side effects of the conventional chemotherapeutic agent(s) and/or speed up recovery from the administration of conventional chemotherapeutic agent(s).

The antioxidative stress compositions of the present invention include, e.g., chemopreventive compositions and immunomodulatory compositions.

Generally, a chemopreventive composition according to the invention comprises an active agent selected from the group consisting of resveratrol, genistein, ellagic acid, curcumin, quercetin, prodrugs, metabolites, salts of any of the foregoing, and mixtures of any of the foregoing ("active agents"). In certain embodiments, resveratrol comprises from about 1% to about 80% of the chemopreventive composition by weight, ellagic acid comprises from about 0.25% to about 20% of the chemopreventive composition by weight, genistein comprises from about 0.5% to about 40% of the chemopreventive composition by weight, curcumin comprises from about 1% to about 80% of the chemopreventive composition by weight; and quercetin comprises from about 1% to about 80% of the chemopreventive composition by weight. The chemopreventive composition may further comprise one or more additional agents selected from the group consisting of lycopene, α-tocopherol, L-selenomethionine, ellagic acid, indole-3-carbinol, sulforaphane, allicin, daidzein, EGCG, prodrugs of any of the foregoing, metabolites of any of the foregoing, and salts of any of the foregoing. The chemopreventive composition may further comprise one or more additional antioxidant(s). The chemopreventive composition of the invention may enhance the immune function of and prolong longevity and/or healthspan of a mammal. The chemopreventive composition may therefore be used in prophylaxis, prevention, and treatment of disorders associated with, caused by or accompanied by a disease involving alteration of gene expression. In certain embodiments, the chemopreventive composition is used, e.g., to prevent, delay the onset, prophylaxis or treatment of cancer, autoimmune disorders, heart disease, inflammatory disorders, bone disorders, bladder function disorders, joint health disorders, arthritis, vision, depression, anxiety, Alzheimer's disease, Parkinson's disease, dementias, diabetes, coronary artery disease, kidney disease, and viral or bacterial infections, etc. In certain embodiments, the chemopreventive composition is used to enhance vibrancy or youthfulness or appearance of a mammal and/or improve energy in a mammal.

An immunomodulatory composition according to the invention generally comprises an active agent selected from the group consisting of resveratrol, genistein, ellagic acid, curcumin, quercetin, prodrugs, metabolites, salts of any of the foregoing, and mixtures of any of the foregoing ("active agents"). In certain embodiments, resveratrol comprises from about 1% to about 80% of the immunomodulatory composition by weight, ellagic acid may comprise from about 0.25% to about 20% of the immunomodulatory composition by weight, genistein comprises from about 0.5% to about 40% of the immunomodulatory composition by weight, curcumin comprises from about 1% to about 80% of the immunomodulatory composition by weight; and quercetin comprises from about 1% to about 80% of the immunomodulatory composition by weight. The immunomodulatory composition may further comprise one or more additional agents selected from the group consisting of lycopene, α-tocopherol, L-selenomethionine, ellagic acid, indole-3-carbinol, sulforaphane, allicin, daidzein, EGCG, prodrugs of any of the foregoing, metabolites of any of the foregoing, and salts of any of the foregoing. The immunomodulatory composition may further comprise one or more additional antioxidant(s).

The immunomodulatory composition may inhibit $H_2O_2$-induced DNA strand breakage in lymphocytes, may have a protective effect on oxidative DNA damage, and may prevent and/or delay oxidative DNA damage. The immunomodulatory composition may also enhance the immune function of and prolong longevity and/or healthspan of a mammal. The immunomodulatory composition may therefore decrease the chances, delay the onset, treat or in prophylaxis of various disorders caused by and/or associated with the oxidative DNA damage. The immunomodulatory composition may also be used to prevent, delay the onset, treatment or prophylaxis of a disease that can be ameliorated through an enhancement to immune function and a disease involving alteration of gene expression. In certain embodiments, the immunomodulatory composition is used, e.g., to prevent, delay the onset, prophylaxis or treatment of cancer, autoimmune disorders, heart disease, inflammatory disorders, bone disorders, bladder function disorders, joint health disorders, arthritis, vision, depression, anxiety, Alzheimer's disease, Parkinson's disease, dementias, diabetes, coronary artery disease, kidney disease, and viral or bacterial infections, etc. In certain embodiments, the immunomodulatory composition is used to enhance vibrancy or youthfulness or appearance of a mammal and/or improve energy in a mammal. In certain embodiments, the immunomodulatory composition is used to prolong longevity and/or healthspan of a mammal (e.g., canine).

In addition, the invention is directed in part to a dog biscuit comprising a chemopreventive composition comprising an active agent selected from the group consisting of resveratrol, genistein, ellagic acid, curcumin, quercetin, prodrugs, metabolites, salts, and mixtures of any of the foregoing. In certain embodiments, the dog biscuit comprises: (i) resveratrol and/or a prodrug of resveratrol and/or a metabolite of resveratrol and/or a salt of resveratrol and/or a salt of the metabolite of resveratrol and/or a salt of the prodrug of resveratrol; (ii) genistein and/or a prodrug of genistein and/or a metabolite of genistein and/or a salt of genistein and/or a salt of the metabolite of genistein and/or a salt of the prodrug of genistein; (iii) ellagic acid and/or a prodrug of ellagic acid and/or a metabolite of ellagic acid and/or a salt of the ellagic acid and/or a salt of the metabolite of the ellagic acid and/or a salt of the prodrug of ellagic acid; (iv) curcumin and/or a prodrug of curcumin and/or a metabolite of curcumin and/or a salt of curcumin and/or the salt of the metabolite of curcumin and/or a salt of the prodrug of curcumin; and (v) quercetin and/or a prodrug or quercetin and/or a metabolite of quercetin and/or a salt of quercetin and/or a salt of the metabolite of the quercetin and/or a salt of the prodrug of quercetin. A dog biscuit may, e.g., comprise from about 0.1 mg to about 2000 mg, from about 100 mg to about 2000 mg, from about 200 mg to about 2000 mg, from about 250 mg to about 2000 mg, from about 300 mg to about 1500 mg, from about 400 mg to about 1500 mg, or from about 500 mg to about 1500 mg of resveratrol per one biscuit; from about 0.1 mg to about 1000 mg, from about 100 mg to about 1000 mg, from about 200 mg to about 1000 mg, from about 250 mg to about 1000 mg, from about 300 mg to about 750 mg, from about 400 mg to about 750 mg, or from about 500 mg to about 750 mg of ellagic acid per one biscuit; from about 0.1 mg to about 1000 mg, from about 100 mg to about 1000 mg, from about 200 mg to about 1000 mg, from about 250 mg to about 1000 mg, from about 300 mg to about 750 mg, from about 400 mg to about 750 mg, or from about 500 mg to about 750 mg of genistein per one biscuit; from about 0.1 mg to about 2000 mg, from about 100 mg to about 2000 mg, from about 200 mg to about 2000 mg, from about 250 mg to about 2000 mg, from about 300 mg to about 1500 mg, from about 400 mg to about 1500 mg, or from about 500 mg to about 1500 mg of curcumin per one biscuit; and from about 0.1 mg to about 2000 mg, from about 100 mg to about 2000 mg, from about 200 mg to about 2000 mg, from about 250 mg to about 2000 mg, from about 300 mg to about 1500 mg, from about 400 mg to about 1500 mg, or from about 500 mg to about 1500 mg of quercetin per one biscuit; or equivalent amounts of metabolites, prodrugs and salts thereof. However, if necessary to achieve a desired effect, a higher or lower amount may be used. In these embodiments, the dog biscuit and/or the chemopreventive composition may further comprise one or more additional agents selected from the group consisting of lycopene, α-tocopherol, L-selenomethionine, ellagic acid, indole-3-carbinol, sulforaphane, allicin, daidzein, EGCG, prodrugs of any of the foregoing, metabolites of any of the foregoing, and salts of any of the foregoing. The dog biscuit and/or the chemopreventive composition may further comprise one or more additional antioxidant(s). Resveratrol, genistein, ellagic acid, curcumin, quercetin, prodrugs, metabolites, salts, and mixtures of any of the foregoing are bioavailable from the dog biscuit and are able to cross enterocytes and enter system blood circulation after oral administration of the dog biscuit. In certain embodiments, the dog biscuit is prepared by a process that does not comprise baking.

In certain embodiments, a dog biscuit comprises a therapeutically effective amount of a combination comprising at least three active agents selected from the group consisting of resveratrol, genistein, ellagic acid, curcumin, quercetin, prodrugs, metabolites, salts, and mixtures of any of the foregoing sufficient to increase expression of CYBB, DUS, GSR, UCP2, and VIMP genes; and downregulate ATOX1, CCL5, EPX, MPV17, PRNP and SOD3 genes in a mammal.

In certain embodiments, a dog biscuit comprises a therapeutically effective amount of a combination comprising at least three or four active agents selected from the group consisting of resveratrol, genistein, ellagic acid, curcumin, quercetin, prodrugs, metabolites, salts, and mixtures of any of the foregoing sufficient to increase monocytes and macrophages in a mammal.

In certain embodiments, a dog biscuit comprises a therapeutically effective amount of a combination comprising at least three active agents selected from the group consisting of resveratrol, genistein, ellagic acid, curcumin, quercetin, prodrugs, metabolites, salts, and mixtures of any of the foregoing sufficient to increase production of IL-10, an inflammatory cytokine that decrease the production of pro-inflammatory cytokines (e.g., TNF-α, IL-1β, and IL-6, in a mammal.

In certain embodiments, a dog biscuit comprises a therapeutically effective amount of a combination comprising at least three active agents selected from the group consisting of resveratrol, genistein, ellagic acid, curcumin, quercetin, prodrugs, metabolites, salts, and mixtures of any of the foregoing sufficient to decrease production of IFN-γ in a mammal.

In certain embodiments, a dog biscuit comprises a therapeutically effective amount of a combination comprising at least three active agents selected from the group consisting of resveratrol, genistein, ellagic acid, curcumin, quercetin, prodrugs, metabolites, salts, and mixtures of any of the foregoing sufficient to decrease production of IL-2 in a mammal.

The invention is also directed in part to a dog biscuit comprising an immunomodulatory composition comprising an active agent selected from the group consisting of resveratrol, genistein, ellagic acid, curcumin, quercetin, prodrugs, metabolites, salts, and mixtures of any of the foregoing. In certain embodiments, the dog biscuit comprises: (i) resveratrol and/or a prodrug of resveratrol and/or a metabolite of resveratrol and/or a salt of resveratrol and/or a salt of the metabolite of resveratrol and/or a salt of the prodrug of resveratrol; (ii) genistein and/or a prodrug of genistein and/or a metabolite of genistein and/or a salt of genistein and/or a salt of the metabolite of genistein and/or a salt of the prodrug of genistein; (iii) ellagic acid and/or a prodrug of ellagic acid and/or a metabolite of ellagic acid and/or a salt of the ellagic acid and/or a salt of the metabolite of the ellagic acid and/or a salt of the prodrug of ellagic acid; (iv) curcumin and/or a prodrug of curcumin and/or a metabolite of curcumin and/or a salt of curcumin and/or the salt of the metabolite of curcumin and/or a salt of the prodrug of curcumin; and (v) quercetin and/or a prodrug or quercetin and/or a metabolite of quercetin and/or a salt of quercetin and/or a salt of the metabolite of the quercetin and/or a salt of the prodrug of quercetin. A dog biscuit may, e.g., comprise from about 0.1 mg to about 2000 mg, from about 100 mg to about 2000 mg, from about 200 mg to about 2000 mg, from about 250 mg to about 2000 mg, from about 300 mg to about 1500 mg, from about 400 mg to about 1500 mg, or from about 500 mg to about 1500 mg of resveratrol per one biscuit; from about 0.1 mg to about 1000 mg, from about 100 mg to about 1000 mg, from about 200 mg to about 1000 mg, from about 250 mg to about 1000 mg, from about 300 mg to about 750 mg, from about 400 mg to about 750 mg, or from about 500 mg to about 750 mg of ellagic acid per one biscuit; from about 0.1 mg to about 1000 mg, from about 100 mg to about 1000 mg, from about 200 mg to about 1000 mg, from about 250 mg to about 1000 mg, from about 300 mg to about 750 mg, from about 400 mg to about 750 mg, or from about 500 mg to about 750 mg of genistein per one biscuit; from about 0.1 mg to about 2000 mg, from about 100 mg to about 2000 mg, from about 200 mg to about 2000 mg, from about 250 mg to about 2000 mg, from about 300 mg to about 1500 mg, from about 400 mg to about 1500 mg, or from about 500 mg to about 1500 mg of curcumin per one biscuit; and from about 0.1 mg to about 2000 mg, from about 100 mg to about 2000 mg, from about 200 mg to about 2000 mg, from about 250 mg to about 2000 mg, from about 300 mg to about 1500 mg, from about 400 mg to about 1500 mg, or from about 500 mg to about 1500 mg of quercetin per one biscuit, or equivalent amounts of metabolites, prodrugs and salts thereof; or equivalent amounts of metabolites, prodrugs and salts thereof. However, if necessary to achieve an adequate level of oxidative DNA damage protection, a higher or lower amount may be used. In these embodiments, the dog biscuit and/or the immunomodulatory composition may further comprise one or more additional agents selected from the group consisting of lycopene, α-tocopherol, L-selenomethionine, ellagic acid, indole-3-carbinol, sulforaphane, allicin, daidzein, EGCG, prodrugs of any of the foregoing, metabolites of any of the foregoing, and salts of any of the foregoing. The dog biscuit and/or the immunomodulatory composition may further comprise one or more additional antioxidant(s).

The invention is further directed to a dietary or nutritional supplement comprising a chemopreventive composition comprising an active agent selected from the group consisting of resveratrol, genistein, ellagic acid, curcumin, quercetin, prodrugs, metabolites, salts, and mixtures of any of the foregoing. In certain embodiments, the supplement comprises: (i) resveratrol and/or a prodrug of resveratrol and/or a metabolite of resveratrol and/or a salt of resveratrol and/or a salt of the metabolite of resveratrol and/or a salt of the prodrug of resveratrol; (ii) genistein and/or a prodrug of genistein and/or a metabolite of genistein and/or a salt of genistein and/or a salt of the metabolite of genistein and/or a salt of the prodrug of genistein; (iii) ellagic acid and/or a prodrug of ellagic acid and/or a metabolite of ellagic acid and/or a salt of the ellagic acid and/or a salt of the metabolite of the ellagic acid and/or a salt of the prodrug of ellagic acid; (iv) curcumin and/or a prodrug of curcumin and/or a metabolite of curcumin and/or a salt of curcumin and/or the salt of the metabolite of curcumin and/or a salt of the prodrug of curcumin; and (v) quercetin and/or a prodrug or quercetin and/or a metabolite of quercetin and/or a salt of quercetin and/or a salt of the metabolite of the quercetin and/or a salt of the prodrug of quercetin and is suitable for administration to humans.

The invention is also directed in part to a dietary or nutritional supplement comprising an immunomodulatory composition comprising an active agent selected from the group consisting of resveratrol, genistein, ellagic acid, curcumin, quercetin, prodrugs, metabolites, salts, and mixtures of any of the foregoing. In certain embodiments, the supplement comprises: (i) resveratrol and/or a prodrug of resveratrol and/or a metabolite of resveratrol and/or a salt of resveratrol and/or a salt of the metabolite of resveratrol and/or a salt of the prodrug of resveratrol; (ii) genistein and/or a prodrug of genistein and/or a metabolite of genistein and/or a salt of genistein and/or a salt of the metabolite of genistein and/or a salt of the prodrug of genistein; (iii) ellagic acid and/or a prodrug of ellagic acid and/or a metabolite of ellagic acid and/or a salt of the ellagic acid and/or a salt of the metabolite of the ellagic acid and/or a salt of the prodrug of ellagic acid; (iv) curcumin and/or a prodrug of curcumin and/or a metabolite of curcumin and/or a salt of curcumin and/or the salt of the metabolite of curcumin and/or a salt of the prodrug of curcumin; and (v) quercetin and/or a prodrug or quercetin and/or a metabolite of quercetin and/or a salt of quercetin and/or a salt of the metabolite of the quercetin and/or a salt of the prodrug of quercetin and is suitable for administration to humans.

The invention is further directed in part to providing a protective effect on oxidative DNA damage and/or delay oxidative DNA damage in mammals (e.g., canines) by administering orally a therapeutically effective amount of the immunomodulatory composition comprising an active agent selected from the group consisting of resveratrol, genistein, ellagic acid, curcumin, quercetin, prodrugs, metabolites, salts of any of the foregoing, and mixtures of any of the foregoing to a mammal (e.g., a canine) on a once-a-day or several times a day basis (e.g., twice-a-day or as several treats during the day). After an oral administration of the immunomodulatory composition to a mammal (e.g., canine), the immunomodulatory composition preferably provides detectable serum levels of, e.g., resveratrol and/or genistein metabolites and/or quercetin and/or metabolites in the mammal. Generally, resveratrol may be administered at a daily dose of from about 0.1 grams/mammal/day to about 2 grams/mammal/day, from about 0.2 grams/mammal/day to about 2 grams/mammal/day, from about 0.3 grams/mammal/day to about 2 grams/mammal/day; from about 0.4 grams/mammal/day to about 2 grams/mammal/day, from about 0.5 grams/mammal/day to about 2 grams/mammal/day, or from about 0.5 grams/mammal/day to about 2 grams/mammal/day; genistein may be administered at a daily dose of from about 0.1 grams/mammal/day to 0.5 grams/mammal/day, from about 0.2 grams/mammal/day to about 0.5 grams/mammal/day, or from about 0.3 grams/mammal/day to about 0.5 grams/mammal/day; ellagic acid may be administered at a daily dose of from 0.1 to 1 grams/mammal/day, from about 0.2 grams/mammal/day to about 1 grams/mammal/day, from about 0.3 grams/mammal/day to about 1 grams/mammal/day; from about 0.4 grams/mammal/day to about 1 grams/mammal/day, from about 0.5 grams/mammal/day to about 1 grams/mammal/day, or from about 0.5 grams/mammal/day to about 1 grams/mammal/day; curcumin may be administered at a daily dose of from 0.1 grams/mammal/day to 2 grams/mammal/day, from about 0.2 grams/mammal/day to about 2 grams/mammal/day, from about 0.3 grams/mammal/day to about 2 grams/mammal/day; from about 0.4 grams/mammal/day to about 2 grams/mammal/day, from about 0.5 grams/mammal/day to about 2 grams/mammal/day, or from about 0.5 grams/mammal/day to about 2 grams/mammal/day; and quercetin may administered at a daily dose of from 0.1 grams/mammal/day to 2 grams/mammal/day, from about 0.2 grams/mammal/day to about 2 grams/mammal/day, from about 0.3 grams/mammal/day to about 2 grams/mammal/day; from about 0.4 grams/mammal/day to about 2 grams/mammal/day, from about 0.5 grams/mammal/day to about 2 grams/mammal/day, or from about 0.5 grams/mammal/day to about 2 grams/mammal/day. However, if necessary to achieve an adequate level of oxidative DNA damage protection, a higher or lower amount may be used.

In addition, the invention is directed in part to a method of preventing, treating and/or delaying an onset of a disease that can be ameliorated through an enhancement to immune function comprising administering to a mammal in need thereof (e.g., canine) a therapeutically effective amount of the chemopreventive composition comprising resveratrol, genistein, ellagic acid, curcumin, quercetin, prodrugs, metabolites, salts of any of the foregoing, and mixtures of any of the foregoing.

The invention is further directed in part to a method of preventing, treating and/or delaying an onset of a disease that can be ameliorated through an enhancement to immune function comprising administering to a mammal in need thereof (e.g., canine) a therapeutically effective amount of the immunomodulatory composition comprising resveratrol, genistein, ellagic acid, curcumin, quercetin, prodrugs, metabolites, salts of any of the foregoing, and mixtures of any of the foregoing.

The invention if further directed in part to a method of preventing, treating, prophylaxis, and/or delaying an onset of a disease involving alteration of gene expression in a mammal (e.g., a canine) comprising administering to a mammal in need thereof a therapeutically effective amount of the immunomodulatory composition comprising an active agent comprising resveratrol, genistein, ellagic acid, curcumin, quercetin, prodrugs, metabolites, salts of any of the foregoing, and mixtures of any of the foregoing.

The invention if further directed in part to a method of preventing, treating, prophylaxis, and/or delaying an onset of a disease involving alteration of gene expression in a mammal (e.g., a canine) comprising administering to a mammal in need thereof a therapeutically effective amount of the chemopreventive composition comprising an active agent comprising resveratrol, genistein, ellagic acid, curcumin, quercetin, prodrugs, metabolites, salts of any of the foregoing, and mixtures of any of the foregoing.

The invention is further directed in part to a method of enhancing vibrancy, youthfulness or appearance of a mammal (e.g., a canine) comprising administering to a mammal in need thereof a therapeutically effective amount of the immunomodulatory composition comprising an active agent consisting of resveratrol, genistein, ellagic acid, curcumin, quercetin, prodrugs, metabolites, salts of any of the foregoing, and mixtures of any of the foregoing.

The invention is also directed in part to a method of enhancing vibrancy, youthfulness or appearance of a mammal (e.g., a canine) comprising administering to a mammal in need thereof a therapeutically effective amount of the chemopreventive composition comprising an active agent consisting of resveratrol, genistein, ellagic acid, curcumin, quercetin, prodrugs, metabolites, salts of any of the foregoing, and mixtures of any of the foregoing.

In addition, the invention is directed in part to a method of improving energy in a mammal (e.g., a canine) comprising administering to a mammal in need thereof a therapeutically effective amount of the immunomodulatory composition comprising an active agent selected from the group consisting of resveratrol, genistein, ellagic acid, curcumin, quercetin, prodrugs, metabolites, salts of any of the foregoing, and mixtures of any of the foregoing.

The invention is directed in part to a method of improving energy in a mammal (e.g., a canine) comprising administering to a mammal in need thereof a therapeutically effective amount of the chemopreventive composition comprising an active agent selected from the group consisting of resveratrol, genistein, ellagic acid, curcumin, quercetin, prodrugs, metabolites, salts of any of the foregoing, and mixtures of any of the foregoing.

The invention is also directed to a method of prolonging longevity of a mammal to a mammal in need thereof a therapeutically effective amount of a composition comprising at least three active agents selected from the group consisting of resveratrol, genistein, ellagic acid, curcumin, quercetin, prodrugs, metabolites, salts of any of the foregoing, and mixtures of any of the foregoing.

The invention is also directed to a method of prolonging healthspan of a mammal to a mammal in need thereof a therapeutically effective amount of a composition comprising at least three active agents selected from the group consisting of resveratrol, genistein, ellagic acid, curcumin, quercetin, prodrugs, metabolites, salts of any of the foregoing, and mixtures of any of the foregoing.

In the methods of the present invention, the antioxidative stress composition (e.g., the chemopreventive or the immunomodulating composition) may be administered orally as part of a conventional solid pharmaceutical dosage form (e.g., as a tablet, capsule, or powder), as a liquid (a solution, an emulsion or a suspension), or as a food additive, a dog chow, or as a dog biscuit or a biscuit-type dosage form. The antioxidative stress composition may be administered once-a-day, twice-a-day, three times a day, four times a day, or as needed (e.g., as part of a treat). In certain embodiments, the composition is administered with an additional active agent. In certain embodiments, the administration would start at the time of full growth of a mammal. For canine, this would be roughly 1 year for smaller breeds, and 2 years for larger breeds. Once started, the administration could continue for a period of from about 3 months to about 20 years.

The invention is further directed in part to a method of preparing an immunomodulatory composition comprising an active agent selected from the group consisting of resveratrol, genistein, ellagic acid, curcumin, quercetin, prodrugs, metabolites, salts of any of the foregoing, and mixtures of any of the foregoing. In certain embodiments at least three active agents selected from the group consisting of resveratrol, genistein, ellagic acid, curcumin, quercetin, prodrugs, metabolites, salts of any of the foregoing, and mixtures of any of the foregoing are incorporated into the immunomodulatory composition.

The invention is also directed in part to a method of preparing a chemopreventive composition comprising an active agent selected from the group consisting of resveratrol, genistein, ellagic acid, curcumin, quercetin, prodrugs, metabolites, salts of any of the foregoing, and mixtures of any of the foregoing. In certain embodiments at least three active agents selected from the group consisting of resveratrol, genistein, ellagic acid, curcumin, quercetin, prodrugs, metabolites, salts of any of the foregoing, and mixtures of any of the foregoing are incorporated into the chemopreventive composition.

The invention is further directed in part to a method of preparing a dog biscuit comprising an immunomodulatory composition comprising an active agent selected from the group consisting of resveratrol, genistein, ellagic acid, curcumin, quercetin, prodrugs, metabolites, salts of any of the foregoing, and mixtures of any of the foregoing. In certain embodiments at least three active agents selected from the group consisting of resveratrol, genistein, ellagic acid, curcumin, quercetin, prodrugs, metabolites, salts of any of the foregoing, and mixtures of any of the foregoing are incorporated into the dog biscuit. Generally, a mix which is free from the immunomodulatory composition is prepared and baked, and then the immunomodulatory composition or the components of the immunomodulatory composition are incorporated into the mix after the mix has been already baked. In certain embodiments, the methods avoid the conventional practice of baking the final product.

In addition, the invention is directed in part to a method of preparing a dog biscuit comprising a chemopreventive composition comprising an active agent selected from the group consisting of resveratrol, genistein, ellagic acid, curcumin, quercetin, prodrugs, metabolites, salts of any of the foregoing, and mixtures of any of the foregoing. Generally, a mix which is free from the chemopreventive composition is prepared and baked, and then the chemopreventive composition or the components of the chemopreventive composition are incorporated into the mix after the mix has been already baked. In certain embodiments, the methods avoid the conventional practice of baking the final product.

It is believed that the combinations of active agents described herein and used in the chemopreventive and immunomodulatory compositions of the invention have not been used and tested prior to the present invention. The combinations of the active agents used in the chemopreventive and immunomodulatory compositions of the invention are therefore new and unique.

As described herein, a number of factors were taken into account in making the selections of the active agents of the chemopreventive and immunomodulatory compositions of the invention. The results reported herein show significant promise and support the notion of providing and perfecting chemopreventive compositions, immunomodulatory compositions and nontoxic dietary supplements can be of value in enhancing the health and well-being of mammals (e.g., canines) and/or improving longevity of mammals (e.g., canines). Of course this would be a meaningful accomplishment for the dog him- or herself, but owners of domestic pets and service animals would also derive great benefit. Further, the work with canines may provide some insight relevant to and may be extrapolated to human disease prophylaxis, prevention and treatment.

Definitions

The term "about" in the present specification means a value within 15% (±15%) of the value recited immediately after the term "about," including the value equal to the upper limit (i.e., +15%) and the value equal to the lower limit (i.e., −15%) of this range. For example, the phrase "about 100" encompasses any numeric value that is between 85 and 115, including 85 and 115.

The term "healthspan" means the length of time in one's life where one is in optimal health. The healthspan may, e.g., be from 1 year to 90 years. For cannines, the healthspan may, e.g., be from 1 year to 25 years.

The term "mean" as used herein is calculated from the data of eight subjects (e.g., canines).

The term "oral administration" encompasses administration with food and without food.

DETAILED DESCRIPTION

Figure 1:
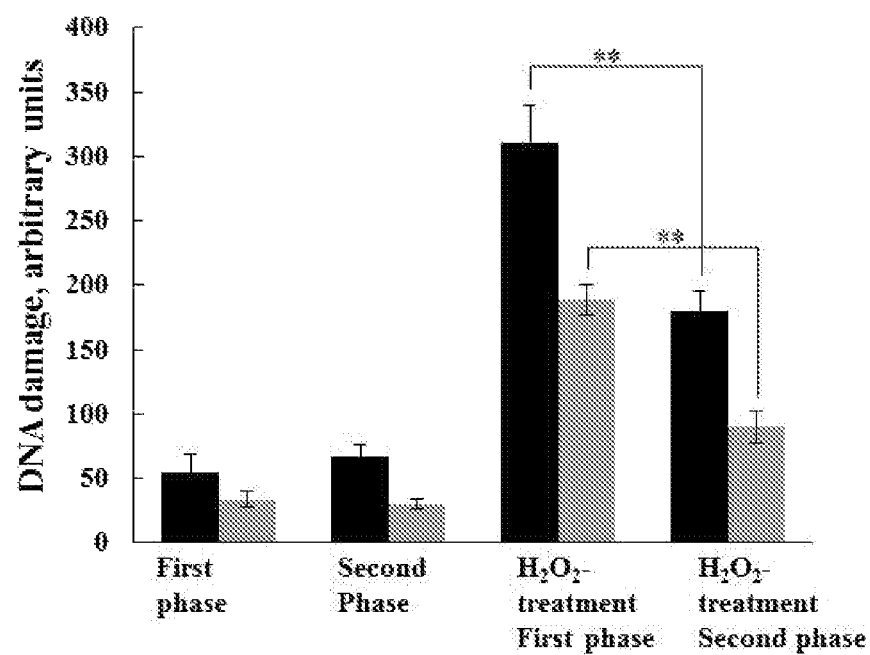
FIG. 1 shows that compositions according to the invention inhibit $H_2O_2$-induced DNA strand breakage in dog lymphocytes. Lymphocytes were washed, suspended in 1% (w/v) LMP agarose and pipetted onto frosted glass microscope slides. For $H_2O_2$ treatment, 10 μl of 1 mM $H_2O_2$ were added to 90 μl of cells in PBS (100 μM final concentration); after 5 min on ice, the cells were collected by centrifugation and applied to slides. Slides were washed three-times with buffer (40 mM HEPES-KOH, 0.1 M KCl, 0.5 mM EDTA, 0.2 mg/ml BSA, pH 8) and incubated for 45 min at 37° C. with either 50 μl buffer or endonuclease III in buffer (1 μg protein/ml). Lymphocytes were stained with SYBR Gold and image analysis was performed using a Leica confocal microscope (FIG. 2). Gray bars are without endonuclease treatment, black bars are with treatment. **$p<0.01$, t-test (n=16).

Oxidative stress causes damage to DNA, RNA, proteins, and other cellular components. Oxidative stress is therefore thought to be a source of many disorders, including, e.g., aging, cancer, autoimmune disorders, heart disease, inflammatory disorders, bone disorders, bladder function disorders, joint health disorders, arthritis, vision, depression, anxiety, Alzheimer's disease, Parkinson's disease, dementias, diabetes, coronary artery disease, kidney disease, and viral or bacterial infections.

Oxidative DNA damage may also adversely affects mammals and may cause cancers and tumors.

Similar to humans, dogs manifest a broad range of cancers such as melanoma, non-Hodgkin lymphoma, osteosarcoma, soft tissue sarcoma, and prostate, mammary, lung and colorectal carcinomas. Approximately 1 in 3 dogs will be diagnosed with cancer during their lifetime, and cancer currently accounts for about half of the deaths of all dogs older than 10 years[2,36].

In situations wherein a tumor is diagnosed and completely excised prior to invasion or metastatic spread, treatment should be definitive. In canine cases, this may involve amputation or radical surgery. However, the situation is even worse when presented with malignant metastatic disease wherein life expectancy is reduced and treatment options are much more limited. Consequently, avoiding all such situations, ostensibly by means of cancer chemoprevention, remains a compelling approach. Despite issues associated with the development of cancer chemopreventive agents, proof-of-principal has been established with drugs such as tamoxifen and finasteride. In nearly every case, for the discovery or development of new cancer chemopreventive agents, laboratory animals (primarily rodents) have been used as models. In more advanced stages of development, additional animals, including canines, are used to establish pharmacokinetics (absorption, distribution, metabolism, and excretion), dosage forms, toxicity, etc. Nonetheless, the ostensible goal of such work is to provide agents for the prevention of cancer with human beings.

In contrast, in the study described below, rather than using the canine as a model for human beings, a goal was also to focus on potential benefits for the animal.

Chemoprevention is an attempt to use nontoxic natural and synthetic substances or their mixtures (e.g., immunomodulatory compositions) to intervene during the relatively early stages of carcinogenesis, before invasive characteristics are manifested[5]. Since carcinogenesis is regarded as a multistep process (e.g., initiation, promotion, progression)[6], in principle, blocking or inhibiting any of these stages could help to prevent or delay tumorigenesis. Further, consistent with epidemiological studies suggesting that a reduced risk of cancer is associated with consumption of vegetables and fruits[7-11], many agents with cancer chemopreventive potential are naturally occurring phytochemicals[12-14]. The etiologic basis of cancer, as well as most age-related diseases, is complex, but it is generally agreed that oxidative stress plays a role[15]. Damage to DNA by oxidative stress is well known[16]. An aim of the study described below was to assess whether dietary intake of some common dietary chemopreventive agents could affect DNA damage and the expression of genes related to oxidative stress with dog lymphocytes.

As described in detail in the Examples section below, detectable serum levels of resveratrol, genistein metabolites, and quercetin (and metabolites) were demonstrated after administration of the immunomodulatory compositions described herein, indicating they cross canine enterocytes and enter blood circulation. This promoted a protective effect on oxidative DNA damage. A hypothesis is that lymphocytes serve as a surrogate for other cell types, and protection from DNA damage is consistent with cancer chemoprevention. The mechanism of protection remains to be defined, but to provide some indication of the effect of the chemopreventive formulation on oxidative stress gene expression, array analysis was performed. Of the up-regulated genes, three belong to oxidative stress responsive group (DUSP1, GSR, VIMP), CYBB is an antioxidant, and UCP2 is related to superoxide metabolism. Many selenoproteins (VIMP) participate in intracellular redox homeostasis and play antioxidant roles[49]. The expression of selenoprotein S (SelS) is related to inflammation and insulin resistance suggesting that SelS may provide a link between inflammation and oxidative stress pathways through its role as an antioxidant[50]. Down-regulated genes are represented by two genes (ATOX1 and MPV17) associated with ROS metabolism, two oxidative stress responsive genes (CCL5 and PRNP), and two others from the antioxidant group (SOD3 and EPX)[36,51-54] (Table 6). Overall, in the context of gene expression, up-regulation (e.g., GSR and UCP2) and down-regulation (e.g., SOD3 and the transcription factor for SOD3, Atox1)[55] may improve antioxidant response or decrease inflammation.

Although, DNA was used as a biomarker in the experiments below, it is believed that the compositions of the invention would provide similar anti-oxidative stress effects in other cellular components, organs and tissues. For example, it is believed that a similar anti-oxidative stress effect is exhibited by the compositions of the invention in, e.g., liver and brain cells.

Of course from a humanitarian point-of-view prevention of canine cancer is gratifying, but owners of pets and service animals would also benefit.

DETAILED DESCRIPTION OF PREFERRED EMBODIMENTS

The following examples illustrate various aspects of the present invention. They are not to be construed to limit the claims in any manner whatsoever. Additional components can be added to the antioxidative stress compositions of the invention, including the chemoprotective compositions and immunomodulatory compositions, based on the judgement of those ordinary experienced in the art.

Example 1

This Example documents the first report to document oral administration of this schedule of combined chemopreventive agents in a canine study.

In enrolling canine pets as the subjects of the study, an objective was to perform a relatively short-term and non-invasive trial. Accordingly, lymphocytic DNA was used as a surrogate biomarker for oxidative stress. As described in the literature, this procedure has been used for assessing both the carcinogenic and anti-carcinogenic potential[17] of test substances and, although lymphocytes are used for the observation, it may be surmised that other cell-types susceptible to carcinogenic insult could mount a similar response[17]. Since the ex vivo protective response of the lymphocyte is evaluated, and the chemopreventive agent is administered orally, it is logical to assume any positive response elicited by the agent would be through an indirect mechanism such as induction of cytoprotective enzymes. Thus, expression profiles with an array designed for canine oxidative stress genes were determined.

During the course of the study, however, an increase in blood monocyte count was observed. This increase was not outside the bounds of what is considered in the normal range by those in the practice of veterinary medicine but, nonetheless, the increase was statistically significant. Bearing in mind the ever increasing role of immunomodulation in cancer prevention or treatment[18], it was decided to perform limited tests to quantify plasma levels of select cytokines. The levels of INF-γ, IL-2, and IL-10 were measured. Members of the interleukin family are involved in cellular defense against viral pathogens playing an important role in responses resulting from oxidative stress. The multifaceted nature of IFN-γ points toward numerous possible therapeutic targets that have the potential of producing significant benefits[19]. Indeed, almost 70% of genes regulated by IFN-γ are also regulated by type I IFN. Of the remaining nonredundant genes affected by IFN-γ, over two-thirds are inducible and the remainder is repressed. Thus, IFN-γ uniquely regulates a significant number of genes related to inflammation and oxidative stress[20]. For many years, the role of IL-2 was established as a cytokine possessing strong pro-inflammatory activity. More recently, however, studies have suggested a role for IL-2 in autoimmune chronic inflammation, suggesting a protective function, when administered at low-doses[21]. IL-10 is an anti-inflammatory cytokine that decreases the production of pro-inflammatory cytokines, such as TNF-α, IL-1β, and IL-6, produced by macrophages or monocytes[22].

In order to conduct the canine trial, a biscuit containing five agents: resveratrol, ellagic acid, curcumin, genistein and quercetin was formulated and manufactured. When administered as single agents, some studies with dogs have been reported in the literature. However, the in-vivo performance of a composition comprising resveratrol, ellagic acid, curcumin, genistein and quercetin is not predictable form the literature. It is also not predictable from the literature how resveratrol, ellagic acid, curcumin, genistein and quercetin will behave when used together in a combination.

For example, plasma levels of genistein were determined in Beagle dogs treated with immediate and extended release tablets[23], dogs were treated with curcumin for the potential therapeutic management of osteoarthritis[24], and quercetin, in combination with clopidogrel, affected the activity of P-glycoprotein[25]. Of course, many preclinical studies have been performed with dogs to assess potential toxicity as a prelude to conducting human trials, such as with resveratrol[26-28].

The chemopreventive formulation devised for this study was based on a variety of considerations. First of all, it was of interest to select agents that (1) are natural products, (2) ostensibly function by pleotropic mechanisms (e.g., inhibit various stages of carcinogenesis such as initiation, promotion, and progression, either singly or in combination), (3) have well-known safety profiles or generally recognized as safe (GRAS) status, (4) have been extensively reported in the scientific literature as chemopreventive agents, and (5) are undergoing or have undergone evaluation in human clinical trials. After thorough evaluation, the following agents were judged as having met these criteria: Resveratrol ('typical' representative dose, 1 g/d/person), lycopiene (15 mg/d), α-tocopherol (50 mg/d), L-selenomethionine (0.2 mg/d), ellagic acid (250 mg/d), indole-3-carbinol (400 mg/d), sulforophane (50 mg/d), quercetin (1 g/d), allicin (3 mg/d), genistein (500 mg/d), daidzein (300 mg/d), curcumin (1 g/d), and EGCG (300 mg/d). At this point in the selection process, some agents were eliminated since adequate quantities may be found in the average diet (e.g., vitamin D, selenium, and α-tocopherol), high expense or issues with general availability (e.g., sulforaphane), poor organoleptic properties (e.g., allicin), or innate difficulty in the biscuit production process.

In the end, a combination including resveratrol, genistein, ellagic acid, curcumin and quercetin was selected for administration at the dosage levels summarized in Table 1:

TABLE 1

Chemopreventive compounds administered to dogs.

| Compound | Source | Purity | Dose (g/dog/day) | Dose in human studies (g/person/day) |
|---|---|---|---|---|
| Resveratrol | Hangzhon Dayangchem Co., Shanghai, China | >95% | 0.5 | 1.0 |
| Ellagic acid | Shandong Juye Sunnyfarm Natural Product CO., LTD, Shandong, China | >99% | 0.125 | 0.25 |
| Genistein | Shandong Juye Sunnyfarm Natural Product CO., LTD, Shandong, China | >95% | 0.250 | 0.5 |
| Curcumin | Shandong Juye Sunnyfarm Natural Product CO., LTD, Shandong, China | >95% | 0.5 | 1.0 |
| Quercetin | Hangzhon Dayangchem Co., Shanghai, China | >95% | 0.5 | 1.0 |

The rationale of the dosage selection is described in Methods (Dog biscuit production). Additional or alternative agents could also have been included in this trial. Nonetheless, in addition to the rationalization presented above, another advantage was that each of the test agents is known to function by pleiotropic mechanisms of action that are relevant to disease prevention. For example, resveratrol has been reported to exert antioxidant, anti-inflammatory, anti-infective, cardioprotective, neuroprotective, antiobesity, and chemopreventive activities[37-40]. It has not been evaluated for cancer chemoprevention in dogs, but analytical work for the determination of trans-resveratrol and derivatives in dog plasma has been described[26,27], as well as preclinical toxicity studies[28]. Ellagic acid occurs in many foods and has antioxidant, antibacterial, antiviral and cancer-preventing properties[41]. It exerts anticancer effects in various cancer cell lines and animal tumor models[42]. Curcumin, a natural polyphenolic antioxidant can mediate a large number of biological responses[44]. Some studies have reported pharmacokinetics in dogs, and stabilizing curcumin with phosphoric acid allows accurate quantitative determinations of curcuminoids in dog plasma[44]. The phytoestrogen genistein is found in soy-based products. It has been suggested that genistein can prevent both prostate and breast cancer[33], particularly in Southeast Asia populations where soy products are consumed at high levels[45]. A LC-MS-MS method has been developed for the determination of genistein in dog plasma following oral administration[23]. Finally, quercetin mediates diverse anti-cancer effects[46]. It is a pleiotropic molecule with limited toxicity on normal cells. Simultaneous targeting of multiple pathways may help to eliminate malignant cells and retard the onset of drug resistance[47].

Example 2

The development and production of a biscuit-type dosage form for relatively large canines presented some challenges since it was important to preserve the integrity of the chemopreventive agents. Thus, the common practice of baking the final product was avoided. During the development phase, many formulations were designed to form durable biscuit-type tablets and changes were made in an effort to reduce bellyband cracks and improve compressibility, compatibility, and flavour. The compaction of each active ingredient was individually tested, which revealed that the compounds themselves aid the compression of the tablets and helped balance the unfavourable compaction characteristics of the other biscuit ingredients.

Another issue that will ultimately be faced in developing a canine chemopreventive product is expense. Based on the quantities and price schedule for the chemopreventive agents purchased and used in this study, the expenditure was $1.65/biscuit. It is difficult to know an amount consumers would find to be acceptable for such as product, but given the high expense associated with treatment (vide supra) and the gratification accompanying disease prevention, an expenditure of this magnitude seems reasonable. Another aspect related to expense is when the dog would begin biscuit consumption. While it is not possible to provide an answer based on existing evidence, since it has been noted that more than half of dogs over 10 years of age are likely to develop cancer[48], it would seem that early administration would be beneficial. One suggestion would be to start consumption at the time of full growth, which would be roughly 1 year for smaller breeds, and 2 years for larger breeds.

Nevertheless, a dog biscuit formulation was devised that contained a combination of resveratrol, genistein, ellagic acid, curcumin and quercetin as active chemopreventive agents. The study design involved two phases. The first phase was to evaluate the palatability and acceptability of the placebo treats. Over a period of three weeks, eight healthy dogs were given the placebo treat twice per day. This assessment was simply to determine whether the dog liked/disliked the taste, texture, etc., of the biscuit, the owner's ease of administration, and the dog's motivation to eat the biscuit. The owners observed the behaviour of the dog to insure the biscuits were well tolerated with and without active ingredients to ensure their delivery. The dogs consumed the biscuits following the prescribed schedule. Some owners used masking techniques.

Blood samples were drawn at the end of the first phase of the study. Following a two-month resting period, the second phase of the study was launched with the same canine subjects. Over a period of three weeks, the diets of the dogs were supplemented with two biscuit treats containing the chemopreventive agents (Table 1), one biscuit by mouth twice daily approximately 12 hours apart each day. After an administration period of three weeks, blood was drawn, and the study was terminated. The comprehensive blood profiles are depicted in Table 2.

TABLE 2

Comprehensive blood profiles.

| | Normal Range | First phase | Second phase |
|---|---|---|---|
| ALB | 2.5-4.4 g/dL | 3.6 ± 0.1 | 3.6 ± 0.1 |
| ALP | 20-150 U/L | 45.1 ± 6.9 | 45.5 ± 6.1 |
| ALT | 10-118 U/L | 53.1 ± 9.4 | 69.1 ± 11.5 |
| AMY | 200-1200 U/L | 511.1 ± 53.6 | 538.6 ± 58.7 |
| TBIL | 0.1-0.6 mg/dL | 0.3 ± 1.0 | 0.3 ± 0 |
| BUN | 7-25 mg/dL | 14.3 ± 1.0 | 15.4 ± 1.2 |
| CA++ | 8.6-11.8 mg/dL | 10.6 ± 0.1 | 10.6 ± 0.1 |
| PHOS | 2.9-6.6 mg/dL | 3.7 ± 0.2* | 4.6 ± 0.1* |
| CRE | 0.3-1.4 mg/dL | 1.1 ± 0.1 | 1.0 ± 0.1 |
| GLU | 60-110 mg/dL | 104.6 ± 4.0 | 104.4 ± 4.5 |

TABLE 2-continued

Comprehensive blood profiles.

|  | Normal Range | First phase | Second phase |
|---|---|---|---|
| NA+ | 138-160 mmol/L | 144.0 ± 0.7 | 145.3 ± 0.3 |
| K+ | 3.7-5.8 mmol/L | 4.7 ± 0.2 | 4.2 ± 0.1 |
| TP | 5.4-8.2 g/dL | 6.7 ± 0.1 | 6.7 ± 0.1 |
| GLOB | 2.3-5.2 g/dL | 3.1 ± 0.1 | 3.3 ± 0.1 |

ALB—albumin; ALP—alkaline phosphatase; ALT—alanine aminotransferase; AMY—amylase; TBIL—total bilirubin; BUN—blood urea nitrogen; CA++—calcium; PHOS—phosphorus; CRE—creatinine; GLU—glucose; NA+—sodium; K+—potassium; TP—total protein; GLOB—globulin.
*p < 0.01.

The owners of these pets transported the dogs to a local veterinary clinic on pre-scheduled days. During these visits, the dogs were weighed and received physical examinations. Venous blood was used for comprehensive serum chemistry profiles and complete blood counts to evaluate organ function and health status, as well as analysis of the chemopreventive agents and assessment of biomarkers. The dogs were maintained by their owners and not housed in any research facility. Special instructions were given as a caution label for biscuits such as keep away from children, store in a refrigerator, may turn urine, feces, saliva yellow, give only as directed, and for animal consumption only. Dogs did not experience any overt toxicity while enrolled in trial. There were no reported changes in bowel habits (diarrhea or constipation), no abdominal bloating, and no gastrointestinal bleeding. However, some minor gastrointestinal effects were reported by the owners. Of the eight canine subjects enrolled in the study, one owner reported decreased appetite while on the biscuit, one owner reported mustard-colored stools while on the biscuit, and three owners reported vomiting following administration of the biscuit that was sporadic.

Haematological parameters were assessed and all values were observed to fall within the normal range attesting to a general state of good health both before and after dietary supplementation.

Comprehensive blood profiles did not show any difference between the first and second phases of the study falling outside of the normal range (Table 2). However, there was a significant increase in the level of serum phosphorous. The reason for this increase is not known. However, a low magnitude change in a single marker wherein the total level still remains in the normal range is not of concern from a veterinary medicine point-of-view. In sum, these data suggest the treatment protocol did not lead to any type of overt toxicity.

The same was true when comparing baseline and post-treatment blood counts (Table 3).

TABLE 3

Complete blood count.

|  | Normal Range | First phase | Second phase |
|---|---|---|---|
| GRA | 3.0-12.0 × 10$^9$/L | 8.4 ± 0.71 | 9.9 ± 0.8 |
| WBC | 6.0-17.0 × 10$^9$/L | 11.1 ± 1.1 | 12.7 ± 1.2 |
| LYM | 1.0-4.8 × 10$^9$/L | 2.2 ± 0.6 | 1.9 ± 0.5 |
| MON | 0.2-1.5 × 10$^9$/L | 0.5 ± 0.1* | 0.9 ± 0.1* |
| RBC | 5.5-8.5 × 10$^{12}$/L | 7.8 ± 0.3 | 7.4 ± 0.3 |
| HGB | 12.0-18.0 g/dL | 16.9 ± 0.6 | 17.0 ± 0.4 |
| HCT | 37.0-55.0% | 49.2 ± 1.9 | 49.3 ± 2.1 |
| MCV | 60-77 fl | 65.6 ± 1.2 | 66.3 ± 1.1 |
| MCH | 19.5-24.5 pg | 23.2 ± 1.0 | 23.0 ± 0.4 |
| MCHC | 31.0-34.0 g/dL | 34.3 ± 0.5 | 34.7 ± 0.7 |

TABLE 3-continued

Complete blood count.

|  | Normal Range | First phase | Second phase |
|---|---|---|---|
| PLT | 200-500 × 10$^9$/L | 233.8 ± 25.5 | 272.6 ± 59.4 |
| MPV | 3.9-11.1 fl | 10.1 ± 0.4 | 9.9 ± 0.4 |

GRA—granulocytes; WBC—white blood cells; LYM—lymphocytes; MON—monocytes; RBC—red blood cells; HGB—hemoglobin; HCT—hematocrit; MCV—mean corpuscular volume; MCH—mean corpuscular hemoglobin; MCHC—mean corpuscular hemoglobin concentration; PLT—platelets; MPV—mean platelet volume;
*p < 0.0001

It is notable, however, when comparing these two groups, there was a statistically significant increase in the number of monocytes after the dogs were given the dietary supplement for the treatment period. Although remaining in the normal range, the monocyte number was found to be significantly higher in the second phase of the study (vide infra) (Table 3).

Serum was isolated from whole blood obtained during the two phases of the trial and analysed by LC-MS/MS. The concentrations of chemopreventive compounds and their metabolites is depicted in FIG. 4:

TABLE 4

Concentrations of chemopreventive compounds and its metabolites in dog serum.

| Compounds | Concentration in serum, ng/ml First phase | Concentration in serum, ng/ml Second phase |
|---|---|---|
| Resveratrol | N/D | 19.3 ± 11.02[a] |
| Resveratrol-3-O-glucuronide | N/D | 64.29 ± 27.24[a] |
| trans-Resveratrol-4'-sulfate | N/D | 44.43 ± 12.23[a] |
| trans-Resveratrol-3-sulfate | N/D | 424.38 ± 80.40[a] |
| cis-Resveratrol-3-sulfate | N/D | 13.63 ± 5.27[a] |
| Resveratrol sulfate total | N/D | 482.43 ± 75.60[a] |
| Ellagic acid | N/D | N/D |
| Genistein | N/D | N/D |
| Genistein-4'-glucuronide | 327.72 ± 211.13[a] | 7083.7 ± 128.18* |
| Genistein-7-glucuronide | N/D | 861.74 ± 329.6 |
| Genistein sulfate | 961 ± 680.3 | 26958.6 ± 2300** |
| Curcumin | N/D | N/D |
| Curcumin glucuronide | N/D | N/D[b] |
| Quercetin | N/D[c] | 2 ± 1 |

N/D—none detected;
[a]one dog did not show any resveratrol, genistein, or respective metabolites, in blood serum, and was excluded from the analysis;
[b]two dogs had concentration of curcumin glucuronide 94 and 31 ng/ml;
[c]three dogs had concentration of quercetin 2, 3 and 2 ng/ml, all others dogs had below detectable level;
*p = 0.0018;
**p = 0.003.

The chemopreventive agents used for this are not normally added to dog chow, and selected dosages were well within safety margins based on previous work conducted mainly in human clinical trials. At the end of this first (placebo) phase of the trial, no resveratrol, resveratrol metabolites, curcumin, curcumin metabolites, or ellagic acid were detected in serum. Genistein-4'-glucuronide (327.7±211.13 ng/mL) and genistein sulfate (961±680.1 ng/mL) were detected in serum of six dogs. It is likely the genistein metabolites were derived from the dog chow, which can contain soybean products. Quercetin levels were below detectable levels in five dogs, but three dogs had quercetin concentrations of 2 or 3 ng/mL. Quercetin occurs in many botanicals and was also probably a constituent of the dog chow (Table 4). After a two-month rest (wash-out) period, the dogs were started on the second phase of the trial by administering two biscuits per day containing the chemopreventive agents. The second phase lasted 3 weeks.

Resveratrol and its metabolites were detected in serum of all dogs but one during the second phase. The most abundant form of resveratrol in dog serum was resveratrol-3-sulfate. Much higher concentrations of genistein metabolites were observed during the second phase (genistein-4'-glucuronide, 7083.74±128.18 ng/ml; genistein-7-glucuronide, 861.74±329.61 ng/ml), with the sulfate being dominant (genistein sulfate, 26958.61±2300 ng/ml) (Table 4). A diet rich in genistein has been associated with lower rates of prostate and breast cancer[33]. When administered orally, genistein is rapidly absorbed and metabolized in humans and animals as are other isoflavones[34]. In the current study, no unconjugated genistein was detected after either the first or the second phases (Table 4). No ellagic acid or curcumin was detected in serum, although curcumin glucuronide was detected at low levels in serum of two dogs after the second phase.

Starting with whole blood from the canine subjects, peripheral blood lymphocytes were isolated. Two measures of DNA damage were evaluated: endogenous DNA damage (DNA damage without $H_2O_2$ exposure) and $H_2O_2$-inducible DNA damage. No statistically significant difference in endogenous lymphocyte DNA damage between the two phases of the study was found (FIG. 1). In dog lymphocytes obtained during the first phase of the trial, $H_2O_2$-induced DNA strand breakage increased from 54±15 to 310±30 units. Remarkably, in second phase of the trial, following administration of the dietary supplement, lymphocyte DNA damage induced by treatment with 100 μM $H_2O_2$ was significantly decreased from 310±30 to 180±16 units (FIG. 1, grey bars). For further confirmation of these data, cell preparations were treated with endonuclease III and the measurements were repeated. Levels of endogenous oxidized pyrimidines did not differ during the first or second phases of the trial. However, $H_2O_2$ treatment increased the level of oxidized pyrimidines, and consumption of the dietary supplement protected lymphocytes against pyrimidine oxidation (FIG. 1, black bars).

To further explore the ramifications of chemopreventive agent administration, total RNA was extracted from lymphocytes, cDNA was generated, and evaluated using a custom made PCR array relevant to dog oxidative stress (Table 5). The oxidative stress related genes custom made for dogs are depicted in Table 5:

TABLE 5

Oxidative stress related genes custom made for dogs.

| GeneBank | Symbol | Description |
| --- | --- | --- |
| NM_001003026 | ALB | Albumin |
| XM_536613 | ALOX12 | Arachidonate 12-lipoxygenase |
| XM_845955 | AOX1 | Aldehyde oxidase 1 pseudogene |
| XM_860950 | APOE | Apolipoprotein E |
| NM_001003119 | ATOX1 | ATX1 antioxidant protein 1 homolog (yeast) |
| XM_845605 | BNIP3L | BCL2/adenovirus E1B 19 kDa protein 3-like |
| NM_001002984 | CAT | Catalase |
| NM_001003010 | CCL5 | Chemokine (C-C motif) ligand 5 |
| NM_001194970 | CCS | Copper chaperone for superoxide dismutase |
| NM_001100290 | CYBA | Cytochrome b-245, alpha polypeptide |
| NM_001100291 | CYBB | Cytochrome b-245, beta polypeptide |
| NM_001077587 | CYGB | Cytoglobin |
| XM_546693 | DHCR24 | 24-dehydrocholesterol reductase |
| NM_001003122 | DUOX1 | Dual oxidase 1 |
| XM_005638367 | DUOX2 | Dual oxidase 2 |
| XM_005619446 | DUSP1 | Dual specificity phosphatase 1 |
| XM_005635675 | EPHX2 | Epoxide hydrolase 2, cytoplasmic |
| XM_548229 | EPX | Eosinophil peroxidase |
| XM_005637294 | FOXM1 | Forkhead box M1 |
| NM_001003080 | FTH1 | Ferritin, heavy polypeptide 1 |
| XM_003431750 | GCLC | Glutamate-cysteine ligase, catalytic subunit |
| XM_005621897 | GCLM | Glutamate-cysteine ligase, modifier subunit |
| NM_001115119 | GPX1 | Glutathione peroxidase 1 |
| NM_001115135 | GPX2 | Glutathione peroxidase 2 (gastrointestinal) |
| NM_001164454 | GPX3 | Glutathione peroxidase 3 |
| NM_001003213 | GPX5 | Glutathione peroxidase 5 (epididymal androgen-protein) |
| NM_001256320 | GPX6 | Glutathione peroxidase 6 (olfactory) |
| XM_005629410 | GPX7 | Glutathione peroxidase 7 |
| NM_001252323 | GPX8 | Glutathione peroxidase 8 (putative) |
| XM_003432097 | GSR | Glutathione reductase |
| XM_005634964 | GSS | Glutathione synthetase |
| NM_001252167 | GSTP1 | Glutathione S-transferase pi 1 |
| XM_003435052 | GSTZ1 | Glutathione transferase zeta 1 |
| XM_005620945 | GTF2I | General transcription factor IIi |
| NM_001194969 | HMOX1 | Heme oxygenase (decycling) 1 |
| NM_001003392 | KRT1 | Keratin 1 |
| XM_005627164 | LOC102155697 | Heat shock 70 kDa protein 1-like |
| XM_844054 | LOC607408 | BCL2/adenovirus E1B 19 kDa interacting protein 3 |
| XM_003433333 | LOC608103 | Methionine sulfoxide reductase A |
| XM_548231 | LPO | Lactoperoxidase |
| XM_005625921 | MB | Myoglobin |
| NM_001252410 | MGST3 | Microsomal glutathione S-transferase 3 |
| XM_847352 | MPO | Myeloperoxidase |
| XM_005630257 | MPV17 | MpV17 mitochondrial inner membrane protein |
| XM_844481 | NCF1 | Neutrophil cytosolic factor 1 |
| NM_001101832 | NCF2 | Neutrophil cytosolic factor 2 |
| NM_001003186 | NOS2 | Nitric oxide synthase 2, inducible |
| XM_005633778 | NOX4 | NADPH oxidase 4 |
| NM_001103218 | NOX5 | NADPH oxidase, EF-hand Ca binding domain 5 |
| XM_848524 | NQO1 | NAD(P)H dehydrogenase, quinone 1 |
| XM_547012 | NUDT1 | Nudix (nucleoside diphosphate moiety X)-type motif 1 |
| XM_003431771 | OXR1 | Oxidation resistance 1 |
| XM_005634251 | OXSR1 | Oxidative-stress responsive 1 |
| XM_534974 | PDLIM1 | PDZ and LIM domain 1 |
| XM_005616288 | PNKP | Polynucleotide kinase 3'-phosphatase |
| NM_001252165 | PRDX1 | Peroxiredoxin 1 |
| XM_542042 | PRDX2 | Peroxiredoxin 2 |
| NM_001256485 | PRDX3 | Peroxiredoxin 3 |
| XM_548896 | PRDX4 | Peroxiredoxin 4 |
| XM_005631542 | PRDX5 | Peroxiredoxin 5 |
| XM_537190 | PRDX6 | Peroxiredoxin 6 |
| XM_543041 | PREX1 | Phosphatidylinositol-3,4,5-dependent Rac exchange factor 1 |
| NM_001013423 | PRNP | Prion protein |
| NM_001003023 | PTGS1 | Prostaglandin-endoperoxide synthase 1 |
| NM_001003354 | PTGS2 | Prostaglandin-endoperoxide synthase 2 |
| XM_005637964 | PXDNL | Peroxidasin homolog (Drosophila)-like |
| XM_543225 | SCARA3 | Scavenger receptor class A, member 3 |
| NM_001115118 | SEPP1 | Selenoprotein P, plasma, 1 |
| XM_546184 | SFTPD | Surfactant protein D |
| XM_850289 | SIRT2 | Sirtuin 2 |
| NM_001003035 | SOD1 | Superoxide dismutase 1, soluble |

TABLE 5-continued

Oxidative stress related genes custom made for dogs.

| GeneBank | Symbol | Description |
|---|---|---|
| XM_533463 | SOD2 | Superoxide dismutase 2, mitochondrial |
| XM_545973 | SOD3 | Superoxide dismutase 3, extracellular |
| XM_005626348 | SQSTM1 | Sequestosome 1 |
| XM_005635344 | SRXN1 | Sulfiredoxin 1 |
| NM_001286859 | STK25 | Serine/threonine-protein kinase 25 |
| NM_001003009 | TPO | Thyroid peroxidase |
| XM_535981 | TTN | Titin |
| XM_533037 | TXNIP | Thioredoxin interacting protein |
| NM_001122673 | TXNRD1 | Thioredoxin reductase 1 |
| XM_845088 | TXNRD2 | Thioredoxin reductase 2 |
| NM_001122778 | TXNRD3 | Thioredoxin reductase 3 |
| NM_001003048 | UCP2 | Uncoupling protein 2 (mitochondrial, proton carrier) |
| NM_001114757 | VIMP | Selenoprotein S |

Of the 84 genes evaluated, the expression of 11 was found to be significantly altered following administration of the dietary supplement. These 11 genes are listed in Table 6:

TABLE 6

Transcriptional regulation of oxidative stress-related genes in dog lymphocytes.

| Gene | Description | Function | Fold Induction | P value |
|---|---|---|---|---|
| Upregulated genes | | | | |
| CYBB | Cytochrome b-245, beta polypeptide (chronic granulomatous disease) | Antioxidant | 2.26 | 0.051 |
| DUSP1 | Dual specificity phosphatase 1 | Oxidative stress responsive gene | 2.68 | 0.023 |
| GSR | Glutatione reductase | Oxidative stress responsive gene | 2.34 | 0.016 |
| UCP2 | Uncoupling protein 2(mitochondrial, proton cattier) | Superoxide metabolism | 3.54 | 0.044 |
| VIMP | Selenoprotein S | Oxidative stress responsive gene | 3.62 | 0.022 |
| Downregulated genes | | | | |
| ATOX1 | ATX1 antioxidant protein | ROS metabolism | −2.83 | 0.048 |
| CCL5 | Chemokine (C-C motif) ligand 5 | Oxidative stress responsive gene | −2.28 | 0.018 |
| EPX | Eosinophil peroxidase | Antioxidant | −2.43 | 0.046 |
| MPV17 | MpV17 mitochondrial inner membrane protein | ROS metabolism | −3.51 | 0.04 |
| PRNP | Prion protein | Oxidative stress responsive gene | −2.85 | 0.047 |
| SOD3 | Superoxide dismutase 3, extracellular | Antioxidant | −3.28 | 0.035 |

Positive values indicates up-regulation; negative values, down-regulation.

Figure 2:
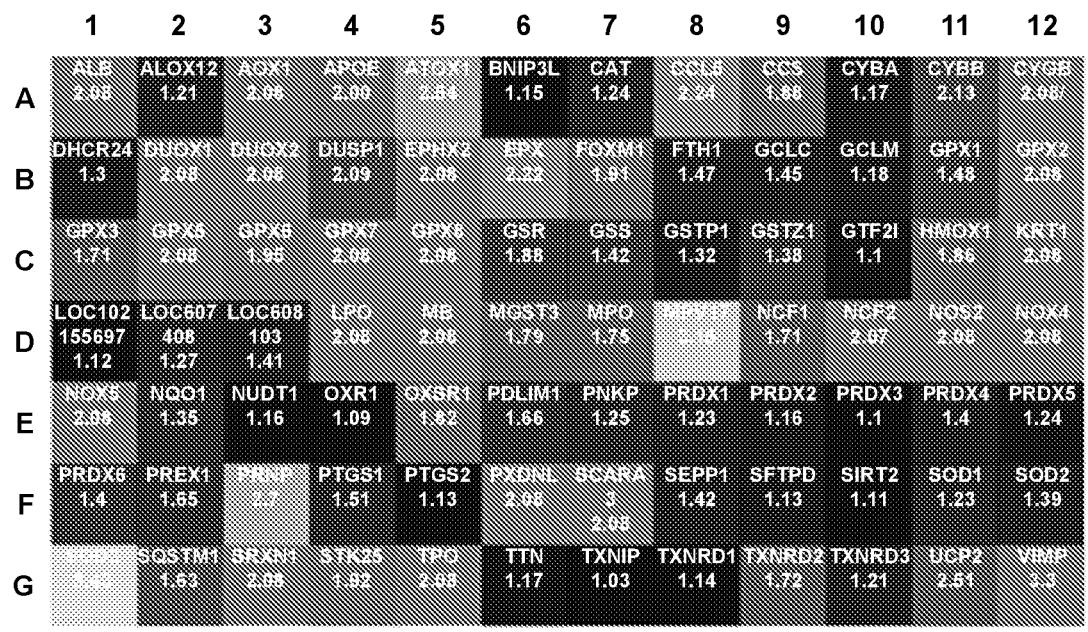
FIG. 2 shows heat map of oxidative stress genes expression in dog lymphocytes. Lymphocytes were isolated from the same dogs after the two phases of the study. RNA was extracted and reverse SyBR Green detection system. The thermal cycling condition was 95° C. for 10 min and then 40 cycles at transcribed to cDNA. Then, cDNA was mixed with RT2 qPCR Master Mix and 25 μl were placed in each well of the array plate. Real-time quantitative PCR was performed using the 95° C. for 15 s followed by 60° C. for 1 min. The fold changes between the two phases of the study were analyzed using the Web-based software provided by SABiosciences (RT2 Profiler PCR Array Data Analysis). Fold changes of 84 genes were determined and presented as heatmaps (Red: up-regulation, green: down-regulation).
Figure 2:
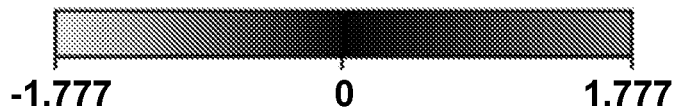

The expression of five genes, including CYBB, DUSP, GSR, UCP2 and VIMP, were significantly increased, whereas those of six genes, including ATOX1, CCL5, EPX, MPV17, PRNP and SODS, were down-regulated (FIG. 2). Among these, VIMP and MPV17 were most highly up- and down-regulated, respectively.

Finally, as noted above, monocyte levels of treated dogs remained in the normal range but were significantly increased. Using plasma obtained from the subjects, the level of IFN-γ was found to be increased by approximately 2-fold during the second phase of the study (13.17±2.66 vs. 26.03±1.94 ng/ml). IL-2 was detected in dog plasma before dietary supplementation (1.12±0.24 ng/ml), but during the second phase, the concentration decreased to below the minimum reliable detectable dose (0.4 ng/ml). During the first phase of the study, the concentration of IL-10 was below the lowest detectable level for this cytokine ELISA (0.12 ng/ml), but significant elevation was detected in the second phase (0.63±0.04 ng/ml) (Table 7). The results are depicted in Table 7:

TABLE 7

Cytokine levels in blood plasma.

| Cytokine | Concentration in plasma, ng/ml First phase | Concentration in plasma, ng/ml Second phase |
|---|---|---|
| IFN-γ | 13.17 ± 2.66 | 26.03 ± 1.94 |
| IL-2 | 1.12 ± 0.24 | BDL |
| IL-10 | BDL | 0.63 ± 0.04 |

Plasma was obtained at the step of lymphocyte isolation. After centrifugation of diluted blood at 340×g for 30 min in a Histopaque gradient, the supernatant (plasma) was collected and frozen at −80° C. ELISA assays were performed as described in the text. The changes in all three parameters are statistically significant using a parametric paired t-test for changes from the first phase of the study to the second ($p<0.001$). The values for BDL (below detectable level) were conservatively assumed to be 0.1 ng/ml, which is the value specified in the manuals for each cytokine kit. Additionally, tests for normality indicate insufficient evidence to assume the changes are not normally distributed (all $p=0.200$ for the Kolmogorov-Smirnov test; $p>0.15$ for the Shapiro-Wilk test).

Chemicals and Reagents

The sources of the chemopreventive agents used in this study are listed in Table 1. Prior to conducting the work, all agents were assessed for purity using LC-UV-MS with a Shimadzu (Kyoto, Japan) IT-ToF high resolution hybrid mass spectrometer equipped with reversed phase HPLC, electrospray and an in-line UV absorbance array detector (Table 1). HPLC-grade methanol and acetonitrile were purchased from Sigma-Aldrich (St. Louis, Mo.) or Thermo-Fisher (Waltham, Mass.). Distilled water, prepared by a Milli-Q water purification system from Millipore (Milsheim, France) was used throughout the study. Endonuclease III from *E. coli*, recombinant, Histopaque-1077, Hank's balanced salt solution (HBSS), dimethylsulfoxide (DMSO), phosphate buffered saline (PBS), and hydrogen peroxide ($H_2O_2$) were purchased from Sigma-Aldrich. Trizol reagent was purchased from Invitrogen™ (Life Technologies, Foster City, Calif.). SYBR® Gold nucleic acid stain was from Life Technologies (Carlsbad, Calif.), Trypan blue solution, 0.4% was purchased from Gibco® (Grand Island, N.Y.). IFN-γ, IL-2 and IL-10 kits were purchased from Ray Biotech. (Norcross, Ga.). Comet assay kit for single cell gel electrophoresis was purchased from Trevigen® (Gaithersburg, Md.). RT$^2$ Profiler™ custom made PCR Array: CAPF12480 related to dog oxidative stress was purchased from QIAGEN-Frederick (SABiosciences, Valencia, Calif.) (Table 5). All other chemicals were of analytical grade.

Canine Subjects

Prior to the initiation of dietary experiments, study protocols were reviewed and approved by the University of Hawaii Institutional Animal Care and Use Committee (IA- CUC). The methods were carried out in accordance with the approved guidelines. At each stage of the study, the dogs were examined by the same veterinarian (JALA).

Dogs were client-owned and participated at the owner's consent. Each dog remained on their individual, normal diet for the duration of the study; no special diet was introduced except for that of the biscuit. Inclusion criteria were as follows: Greater than 1 year of age; in the weight range of 50-100 pounds; essentially healthy. Any dog not meeting the inclusion criteria was excluded from the study. The eight study participants ranged in age from 2-12 y (median: 6 y), and in weight from 49.4-72.4 lbs (median: 60.4 lbs; 27.45 kg). The participants were of the following breeds: Golden retriever, Border collie mix, New Finland/English setter mix, Golden retriever/Labrador mix, Labrador/Australian shepherd mix, German shepherd/Labrador mix, Labrador, and Labrador mix.

Dog Biscuit Production

The following assumptions were made in the design phase of the study. First of all, in the more typical situation of converting an animal dose (mg/kg) to a human-equivalent dose (mg/kg), one approach is to divide the animal dose by a factor of $1.8^{62}$. Here, being presented with doses taken by human beings, our goal was to determine a canine dose by extrapolation. For example, a value of 1 g/day/person was selected for resveratrol, or around 16 mg/kg body weight. Applying the conversion factor of 1.8, the canine dose becomes 29 mg/kg, and assuming a body weight of 20-30 kg, the daily dosage would be 580-870 mg. These are very rudimentary conversions, and the safety profiles of the test agents are extremely broad, but weighing on the side of being conservative, a daily dose of 500 mg was selected. A similar approach was used for selecting the dosages for the remaining chemopreventive agents used in this study.

For the formulation of dog biscuits, the base mix contained wheat flour (0.62 kg), corn meal (0.17 kg), eight beef bouillon cubes (4.136 g each), and water (225 ml). Dry ingredients were weighed out and added to a planetary mixer and mixed for three minutes. Water was added dropwise over 75 seconds. The mixture was then baked for 60 min at 60° C. yielding a total batch weight of 0.716 kg. The completed base mix was cooled, packaged in plastic bags, and refrigerated. The mixture of chemopreventive compounds was slugged on a Carver F press. The granules resulting from gently hand grinding in a mortar and pestle were then mechanically blended with core material and excipients, and checked for flow ability in a full size hopper. The granules were then mixed with 250 g of core base mix and excipients then run through the F press again. This required agitation, but the resulting biscuits were consistent in weight ranging from 1.4 to 1.5 g. The samples were checked for compatibility on the Carver press at 10,000 psi with a 1 min dwell time. As a result, the following cancer chemopreventive agents were included in the mixture (mg per one biscuit): resveratrol, 250; ellagic acid, 63; genistein, 125; curcumin, 250; quercetin, 250. Placebo biscuits did not contain the chemopreventive agents.

Serum and Plasma Preparation and Complete Blood Counts

Whole blood (6 ml) was collected from each canine subject at the end of the first and second phases of the study. Blood was obtained by venipuncture from either the cephalic or jugular vein (typically with an 18-20 gauge needle attached to a 10 ml syringe). Manual restraint and aseptic techniques were used. The blood from each dog was placed in labelled collection tubes (2 ml in lavender EDTA collection tubes, 1 ml in green lithium heparin collection tubes, and 3 ml in red silicone coated tubes). The lavender tubes were inverted and used to run Complete Blood Counts (CBC) and for isolation of lymphocytes, the green tubes were inverted and used to run Comprehensive Chemistry Blood Profiles (CCBP), and the blood within the red tubes were allowed to clot, and then centrifuged for 15 min at 3400 rpm to obtain serum. The serum was frozen prior to analysis by LC-MS/MS. The CBC and CCBPs were run on Abaxis™ VetScan machines, particularly the VS2 and HMS.

LC-MS and LC-MS/MS

Liquid-liquid extraction was used to prepare dog serum for mass spectrometric analysis. Briefly, 300 µl of serum was mixed with 900 µl of ice-cold acetonitrile. Each sample was vortex mixed for 20 sec and then centrifuged for 10 min at 13,000×g. The supernatant was removed and evaporated to dryness under a stream of nitrogen, and each extract was reconstituted in 100 µl of acetonitrile/water (20:80, v/v) prior to analysis using LC-MS/MS.

Analyses of resveratrol and its metabolites, quercetin and genistein were carried out using a Shimadzu IT-ToF mass spectrometer for purity confirmation and a Shimadzu LCMS-8050 triple quadrupole mass spectrometer for quantitation. Both instruments were equipped with negative ion electrospray and interfaced to Shimadzu HPLC systems (Prominence Ark. or Nexera, respectively). A Waters (Milford, Mass.) XBridge $C_{18}$ column (2.1×100 mm; 2.5 µm) was used for chromatographic separations. The solvent system consisted of a 5-min linear gradient from 10% to 90% acetonitrile in water at a flow rate of 400 µl/min. The injection volume was 10 µl.

For quantitative analysis, selected reaction monitoring (SRM) was used with collision-induced dissociation and argon as the collision gas. Deprotonated molecules of each analyte were used as precursor ions, and the SRM transitions of the two most abundant product ions were selected as quantifiers and qualifiers, respectively. In some cases, only one SRM transition (quantifier) was used due to the low abundances of other fragment ions. For resveratrol, the SRM transitions were m/z 227 to 143 and m/z 227 to 185. The SRM transitions of m/z 403 to 227 and m/z 403 to 143 were used for resveratrol glucuronide, and m/z 307 to 227 and m/z 307 to 143 were used for resveratrol sulfate. The SRM transitions for genistein were m/z 269 to 89 and m/z 269 to 187, and the SRM transitions for genistein glucuronide and genistein sulfate were m/z 445 to 269 and m/z 349 to 269, respectively. Quercetin was measured using the SRM transitions of m/z 301 to 151 and m/z 301 to 179, and its glucuronide and sulfate metabolites were monitored using the transitions of m/z 477 to 301 and m/z 381 to 301, respectively. Synthetic isopentyl naringenin was used as an internal standard (SRM transition m/z 341 to 119). Although SRM transitions for curcumin (m/z 367 to 134 and m/z 367 to 217), curcumin glucuronide (m/z 543 to 367), curcumin sulfate (m/z 447 to 367), and ellagic acid (m/z 301 to 229) were monitored, no signals were obtained for these compounds in the study samples.

Lymphocyte Isolation

For the isolation of canine lymphocytes, the procedure of Strasser et al.[63] was followed. Two milliliters of blood in lavender EDTA collection tubes were placed on ice and delivered to the research laboratory. Cold Histopaque-1077 (2 ml; Sigma-Aldrich, St. Louis, Mo.) solution was carefully place in 15 ml conical centrifugal polypropylene tubes (Becton and Dickinson). Blood was diluted with sterile PBS (1:1) at room temperature, layered carefully onto the Histopaque-1077, and centrifuged at 340×g for 30 min using a swinging-bucket rotor. Centrifugation was terminated without applying a brake. The supernatant (plasma) was frozen at −80° C., and the opaque bands at the interface between plasma and Histopaque-1077 containing lymphocytes were collected carefully with a siliconized Pasteur pipet and transferred to separate conical centrifugal tubes. Lymphocytes were washed with 10 ml of Hank's balanced salt solution (HBSS) (two-times; 10 min at room temperature; 300×g). Cells were counted and frozen as aliquots immediately using preservation media (9 mL FBS mixed with 1 ml sterile dimethyl sulfoxide) at approximately −1° C./min in an isopropyl freezing container at −80° C. before storage in liquid nitrogen. The average yield was $10^6$ lymphocytes from 1 ml of dog blood. Lymphocytes were distinguished from monocytes and neutrophils by visual inspection. Contamination did not exceed 3%.

In addition, lymphocytes were distinguished from monocytes and neutrophils by microscopic inspection after Diff-Quik staining of fixed cell smears. The nucleus of the lymphocyte appears as a dense formation that is oval-round and deep purple. Cytoplasm is clear, with no granules, and only sparse vacuoles. The monocyte nucleus is horse-shoe shaped and not as dense; it is pale purple, lacy and spongy. The cytoplasm appears grey with numerous vacuoles. The nuclei of neutrophils have several lobes, and these cells do not layer above Histopaque-1077 due to their density. Based on this visual inspection, contamination of lymphocytes with other cell types was found to be less than 3%.

LC-MS and LC-MS/MS. Liquid-liquid extraction was used to prepare dog serum for mass spectrometric.

Cell Viability

Cell viability was determined using the Trypan blue exclusion test. Trypan blue stock solution (0.4%; 10 µl) was added to isolated lymphocytes (90 µl) and immediately loaded onto a hemocytometer. The number of blue stained cells and the number of total cells was determined by visual inspection. Viability was found to be 90.2±8.3%. Since lymphocytes are readily assessable and play important roles in both the physiological and pathological processes, it is reasonable to regard them as a useful indicator for oxidative DNA damage[64], in humans[65] as well as canines[66] and other species[17].

Cytokine Measurements in Plasma

Following the instructions provided by the manufacturer, levels of IFN-γ, IL-2 and IL-10 in dog plasma were determined with ELISA kits purchased from Ray Biotech (Norcross, Ga.). The ELISA kits were designed for in vitro quantitative measurement of samples in serum, plasma, cell culture supernatant. The assays employ antibodies specific for canine cytokines. Assays were validated for each measurement using a set of calibration standards.

Comet Assay

Figure 3:
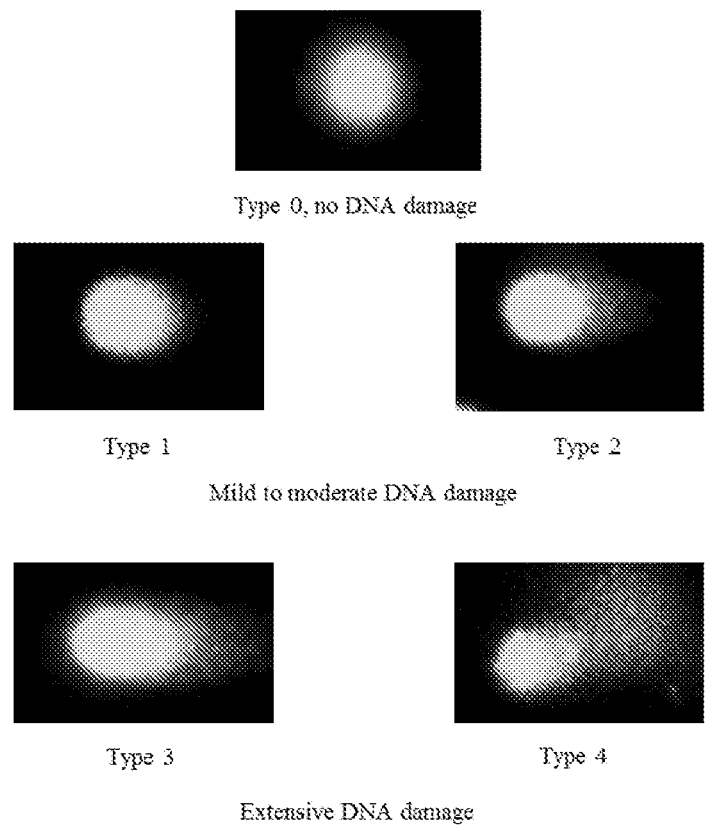
FIG. 3 shows comet images of lymphocyte DNA damage from control dogs and dogs receiving dietary supplementation. Frozen lymphocytes were thawed, centrifuged, resuspended in PBS and incubated 5 min on ice with 100 μM $H_2O_2$. DNA damage was measured with the comet assay. Type 0, no DNA damage detected in lymphocytes; type 1 and 2 presented at the most in lymphocytes with endogenous DNA damage; type 3 and 4 are in $H_2O_2$ or endonuclease III inducible DNA damage.

The extent of DNA damage in peripheral blood lymphocytes was measured by single-cell gel electrophoresis (the alkaline comet assay)[17,67,68]. Cells embedded in agarose on a microscope slide are lysed with detergent and high salt to form nucleoids containing supercoiled loops of DNA linked to the nuclear matrix. DNA was allowed to unwind under alkaline conditions. Breaks in the DNA molecule disrupt its complex supercoiling allowing free DNA loops to migrate towards the anode during electrophoresis. DNA damage to the cells can be thus visualized as "comets" (FIG. 3). Two measures of DNA damage in lymphocytes were evaluated: endogenous DNA damage (DNA damage without ex vivo $H_2O_2$ exposure) and $H_2O_2$-inducible DNA damage. Analysis was performed according to the method of Singh et al.[68] and Tice et al.[69] with some modifications[70]. A Trevigen® Comet assay kit (Gaithersburg, Md.) was used for single cell gel electrophoresis. Cells were immobilized in a bed of low melting agarose on a Trevigen CometSlide™. A cell suspension containing $1\times10^5$ cells per ml was combined with 500 µl of LMAgarose providing agarose in a ratio 1:10 for optimal results when spread at 50 µl of mixture per slide well. Slides were covered with a glass cover-slip and left at 4° C. in the dark for 10 min. Increasing gelling time to 30 min improved adherence of the samples. Slides were placed for a minimum of one hour in lysis solution (the buffer formulation is proprietary) to remove membranes, cytoplasm and nuclear proteins. The CometSlide™ was then immersed in alkaline unwinding solution for 20 min at room temperature or 1 h at 4° C. in the dark. Horizontal electrophoresis was conducted at 21 volts for 30 min at 4° C. After neutralizing, the gels were soaked in 70% ethanol for 5 min and dried at 37° C. for 10-15 min. Gels were treated with 100 µl SYBR® Gold nucleic acid stain (Life Technologies) and viewed by fluorescent microscopy using a Leica TCS SPE confocal microscope (Leica, UK) at Abs/Em 496/540 nm. Slides were examined at 400× magnification using image analysis software (CometScore from TriTek Corp., Sumerduck, Va.).

From each replicate slide, 50 nuclei were scored and the percentage of tail DNA intensity was used to evaluate the extent of DNA migration and damage[66]. Fluorescently stained nucleoids from each gel were assessed and classified according to the relative intensity of fluorescence in the tail undamaged) (FIG. 3). Each cell was visually scored according to the following criteria: no damage (type 0), mild to moderate damage (type 1 and 2), and extensive DNA damage (type 3 and 4). Under the assay conditions used in this experiment, the intensity of comet tails reflects electrophoretic migration of DNA resulting from strand breaks. This parameter was used as arbitrary units. Tail length tends to increase rapidly with dose at low levels of damage, but soon reaches its maximum. Tail moment units were not used, since it combines the information of tail length and tail intensity, but suffers from lack of linearity[66]. To detect specifically oxidized pyrimidines in DNA, recombinant bacterial DNA repair enzyme, endonuclease III from *E. coli*, was used[65]. This provides a specific and sensitive measure of oxidative DNA damage[65]. The slides were washed three-times after lysis for 5 min at 4° C. with buffer (40 mM HEPES-KOH, 0.1 M KCl, 0.5 mM EDTA, 0.2 mg/ml BSA, pH 8). After blotting dry with tissue paper, the gels were incubated for 45 min at 37° C. with either 50 µl buffer or endonuclease III in buffer (1 µs protein/mL)[64]. All samples were analysed in duplicate. Levels of endogenous oxidized pyrimidines demonstrated a similar pattern as endogenous DNA damage, i.e., no significant difference between first and second phases (FIG. 1).

DNA damage inflicted by $H_2O_2$

In the next set of experiments, hydrogen peroxide was employed as an oxidant. It has been shown that hydrogen peroxide causes a dose-dependent increase in DNA strand breaks in human and dog lymphocytes[66,71]. Lymphocytes were thawed, mixed with PBS, centrifuged at 200×g for 3 min at 4° C., and resuspended in PBS at $2\times10^6$ cells/ml. For $H_2O_2$ treatment, 10 µl of 1 mM $H_2O_2$ were added to 90 µl of cells in PBS. After 5 minutes on ice, the cells were collected by centrifugation at 300×g for 10 min and analysed by single cell gel electrophoresis.

Gene Expression Analysis

To explore the potential mechanism underlying the protection effect of the dietary supplement on lymphocytes damage caused by $H_2O_2$, a cDNA microarray was employed. For this analysis, RNA was isolated from dog lymphocytes and reverse transcribed to cDNA. The same amount of cDNA with $RT^2$ qPCR master mix (25 µl) was placed in each well and subjected to real-time PCR reaction with the SYBR Green detection system. Using the ΔΔCt method changes in gene expression between the two phases of the study employing Web-based software from SABiosciences ($RT^2$ Profiler PCR array data analysis) were analyzed.

The procedure follows. Total RNA was extracted from $1\text{-}2\times10^6$ lymphocytes using Trizol reagent (Invitrogen™) according to the method of Chomczynski and Sacchi[72]. Isolated RNA was dissolved in RNase-free water and the quality and quantity were measured using a BioSpec-nano spectrophotometer (ShimadzuBiotech). cDNA was generated from total RNA by reverse transcription using a $RT^2$ First strand kit from Qiagen on an ABI 7300 thermocycler (Applied Biosystems Inc.). cDNA was applied to a $RT^2$ profiler custom made PCR Array related to dog oxidative stress (Table 5) following the manufacturer's instructions (QIAGEN-Frederick, SABiosciences). Samples were run in triplicate to ensure amplification integrity. Expression levels were analysed with each sample[73,74]. Fold-changes of genes were determined and visualized as heatmaps (red: up-regulation, and green: down-regulation) (FIG. 2).

Statistical Analysis

Results are presented as means±SE. Data representing the various groups were compared using the Student's t-test and the level of $P<0.05$ was considered as significantly different. Cytokine data were subjected to the Kolmogorov-Smirnov and Shapiro-Wilk tests of normality. Other statistical considerations are described in the text or tables.

CONCLUSION

As explained above, in order to assess the general health of the animals, comprehensive blood profiles were examined during the first and second phases of the study. No changes of veterinary concern were observed, but the population of monocytes was found to be increased after the dogs were given the dietary supplement for the treatment period. Previously, it has been shown in dog studies that monocytes and macrophages are the first cell types responding to neoplastic stimulus, acting through the synthesis of IFN-γ and interleukins[56]. Resveratrol, one of the most studied ingredients in our supplementation, decreases oxidative burst capacity and changes cytokine production in dogs[57]. Thus, as described above, the plasma concentration of select cytokines were assessed, and modulation was observed.

The cytokine levels in this study were similar to other studies using ELISA methodology[58]. At this point in time, interpretation of the data is simply based on the observed changes. Interestingly, however, IL-10, elevated in this study, is an anti-inflammatory cytokine that decreases the production of pro-inflammatory cytokines, such as TNF-α, IL-1β, and IL-6[22]. IFN-γ, the concentration of which was possibly increased by CYBB up-regulation[59,60] (Table 6), affects numerous therapeutic targets with the potential of producing significant benefits. Using more sensitive methodology, reduction of IL-2 concentrations has been considered significant[61], and here diminution to a level below the limit of detection is reported. Taking into consideration the potential importance of immunomodulation in disease prevention[18], based on these preliminary findings, additional studies would be of interest. Since it is likely that immunomodulatory mechanisms are distinct from oxidative mechanisms protecting DNA from damage, the implications of the described study are multifaceted.

BIBLIOGRAPHY

1. Adrian, J. A., Deliramich, A. N.& Frueh, B. C. Complicated grief and posttraumatic stress disorder in humans' response to the death of pets/animals. *Bul. Menninger Clin.* 73, 176-187 (2009).
2. Langdon, S. P. Animal modelling of cancer pathology and studying tumor response to therapy. *Curr. Drug Targets* 13, 1535-1547 (2012).
3. Tilley, L. P. et al. (2007) Osteosarcoma. In: Blackwell's five-minute veterinary consult: canine and feline (ed. Blackwell Publishing) 1006-1007 (Ames, 2007).
4. Burry, M. Managing costs of cancer treatment for dogs. PetCareRx. (2013) Available at: https://www.petcarerx-.com/article/managing-costs-of-eancer-treatment-for-dogs/1232) (accessed on Feb. 4, 2016).
5. Sporn, M. B. & Suh, N. Chemoprevention: an essential approach to controlling cancer. *Nat. Rev. Cancer* 2, 537-43 (2002).
6. Barrett, J. C. Mechanisms of multistep carcinogenesis and carcinogen risk assessment. *Environ. Health Perspect.* 100, 9-20 (1993).
7. Kurahashi, N. at al. JPHC Study Group. Vegetable, fruit and antioxidant nutrient consumption and subsequent risk of hepatocellular carcinoma: a prospective cohort study in Japan. *Br. J Cancer.* 100, 181-184 (2009).
8. Tantamango-Bartley, Y., Jaceldo-Siegl, K., Fan, J. & Fraser, G. Vegetarian diets and the incidence of cancer in a low-risk population. *Cancer Epidemiol Biomarkers Prev.* 22, 286-294 (2012).
9. Orlich, M. J. et al. Vegetarian dietary patterns and the risk of colorectal cancers. *JAMA Intern. Med.* 175, 767-776 (2015).
10. Benetou, V. et al. Vegetables and fruits in relation to cancer risk: evidence from the Greek EPIC Cohort Study. *Cancer Epidemiol. Biomarkers Prev.* 17, 387-392 (2008).
11. Cohen, J. H., Kristal, A. R. & Stanford, J. L. Fruit and vegetable intakes and prostate cancer risk. *J. Natl. Cancer Inst.* 92, 61-68 (2000).
12. Pezzuto, J. M. Plant-derived anticancer agents. *Biochem. Pharmacol.* 53, 121-133 (1997).
13. Gullett, N. P. et al. Cancer prevention with natural compounds. *Semin. Oncol.* 37, 258-281 (2010).
14. Surh, Y.-J. Cancer chemoprevention with dietary phytochemicals. *Nat. Rev. Cancer* 3, 768-780 (2003).
15. Pezzuto, J. M., Park, E. J. & Park, E.-J. *Encyclopedia of Pharmaceutical Technology* (Taylor & Francis, 2013).
16. Cerutti, P. Prooxidant states and tumor promotion. *Science* 227, 375-381 (1985).
17. Collins, A. R. The comet assay for DNA damage and repair. *Mol. Biotech.* 26, 249-261 (2004).
18. Antonia, S. J., Larkin, J. & Ascierto, P. A. Immuno-oncology combinations: a review of clinical experience and future prospects. *Clin Cancer Res.* 20, 6258-6268 (2014).
19. Hertzog, P. et al. Systems biology of interferon responses. *J. Interferon Cytokine Res.* 31, 5-11 (2011).
20. Billiau, A. et al. Interferon-gamma: a historical perspective. *Cytokine growth factor rev.* 20, 97-113 (2009).
21. Kosmaczewska, A. Low-dose interleukin-2 therapy: a driver of an imbalance between immune tolerance and autoimmunity. *Int. J. Mol. Sci.* 15, 18574-18592 (2014).

22. Kawaratani, H. et al. The effect of inflammatory cytokines in alcoholic liver disease. Mediators of Inflammation. (Hindawi Publishing Corporation, 2013).
23. Feng, D., Qiu, F., Tong, Z. & Xie, C. Oral pharmacokinetic comparison of different genistein tablets in Beagle dogs. *J. Chromat. Science* 51, 335-340 (2013).
24. Colitti, M., Gaspardo, D., Dellapria, A., Scaini, C. & Stefanon, B. Transcriptome modification of white blood cells after dietary administration of curcumin and nonsteroidal anti-inflammatory drug in osteoarthritic affected dogs. *Vet. Immunol. Immunopathol.* 147, 136-146 (2012).
25. Lee, J. H., Shin, Y. J., Oh, J. H. & Lee, Y. J. Pharmacokinetic interactions of clopidogrel with quercetin, telmisartan, and cyclosporine A in rats and dogs. *Arch. Pharm. Res.* 35, 1831-1837 (2012).
26. Muzzio, M. et al. Determination of resveratrol and its sulfate and glucuronides metabolites in plasma by LC-MS and their pharmacokinetics in dogs. *J. Pharm. Biomed. Anal.* 59, 201-208 (2012).
27. Maier-Slamon, A. et al. Hepatic glucuronidation of resveratrol: interspecies comparison of enzyme kinetic profiles in human, mouse, rat, and dog. *Drug Metab. Pharmacokinet.* 26, 364-373 (2011).
28. Johnson, W. D. et al. Subchronic oral toxicity and cardiovascular safety pharmacology studies of resveratrol, a naturally occurring polyphenol with cancer preventive activity. *Food Chem. Toxicol.* 49, 3319-3327 (2011).
29. Chen, T. et al. Randomized phase II trial of lyophilized strawberries in patients with dysplastic precancerous lesions of the esophagus. *Cancer Prev. Res.* 5, 41-50 (2011).
30. Gupta, S. C., Patchva, S. & Aggarwal, B. B. Therapeutic roles of curcumin: lessons learned from clinical trials. *AAPS Journal* 15, 195-218 (2013).
31. Russo, M. et al. The flavonoid quercetin in disease prevention and therapy: facts and fancies. *Biochem. Pharmacol.* 83, 6-15 (2012).
32. Sporn, M. B. Combination chemoprevention of cancer. *Nature* 287, 107-108 (1980).
33. Russo, et al. Understanding genistein in cancer: The "good" and the "bad" effects: A review. *Food Chem.* 196, 589-600 (2016).
34. Barnes, S. et al. The metabolism and analysis of isoflavones and other dietary polyphenols in foods and biological systems. *Food Funct.* 2, 235-244 (2011).
35. Patterson, S. L., Colbert Maresso, K. & Hawk, E. Cancer chemoprevention: successes and failures. *Clin. Chem.* 59, 94-101 (2013).
36. Baek, S. J., McEntee, M. F. & Legendre, A. M. Review paper: cancer chemopreventive compounds and canine cancer. *Vet. Pathol.* 46, 576-588 (2009).
37. Pezzuto, J. M. et al. The phenomenon of resveratrol: redefining the virtues of promiscuity. *Ann. N.Y. Acad. Sci.* 1215, 123-130 (2011).
38. Calamini, B. K. et al. Pleiotropic mechanisms facilitated by resveratrol and its metabolites. *Biochem. J.* 429, 273-282 (2010).
39. Park, E.-J & Pezzuto, J. M. The pharmacology of resveratrol in animals and humans. *Biochim. Biophys. Acta* 1852, 1071-1113 (2015).
40. Aggarwal, B. B. & Shishodia, S. (eds.), *Resveratrol in Health and Disease*, New York, N.Y.: Marcel Dekker, Inc., pp. 679 (2006).
41. Zhang, H. M. et al. Research progress on the anticancer actions and mechanisms of ellagic acid. *Cancer Biol. Med.* 11, 92-100 (2014).
42. Priyadarsini, R. V. et al. Gene expression signature of DMBA-induced hamster buccal pouch carcinomas: modulation by chlorophyllin and ellagic acid. *PLoS One* 7, e34628 (2012).
43. Goel, A. et al. Curcumin as "Curecumin": from kitchen to clinic. *Biochem. Pharmacol.* 75, 787-809 (2007).
44. Helson, L. et al. Infusion pharmacokinetics of Lipocurc™ (liposomal curcumin) and its metabolite tetrahydrocurcumin in Beagle dogs. *Anticancer Res.* 32, 4365-4370 (2012).
45. Barnes, S. et al. Soy isoflavonoids and cancer prevention. Underlying biochemical and pharmacological issues. *Adv. Exp. Med. Biol.* 401, 87-100 (1996).
46. Cai, X. et al. Bioavailability of quercetin: problems and promises. *Curr. Med. Chem.* 20, 2572-2582 (2013).
47. Russo, G. L. et al. Quercetin: a pleiotropic kinase inhibitor against cancer. *Cancer Treat. Res.* 159, 185-205 (2014).
48. Webster, J. D. et al. Recommended guidelines for the conduct and evaluation of prognostic studies in veterinary oncology. *Vet. Pathol.* 48, 7-18 (2011).
49. Zhao, Y. et al. Effect of selenoprotein S on oxidative injury in human endothelial cells. *J. Transl. Med.* doi: 10.1186/1479-5876-11-287 (2013).
50. Jiang, F., Zhang, Y., Dusting, G. J. & Sibley, D. R. NADPH oxidase-mediated redox signaling: roles in cellular stress response, stress tolerance, and tissue repair. *Pharmacol. Rev.* 63, 218-242 (2011).
51. Tchen, C. R. et al. Glucocorticoid regulation of mouse and human dual specificity phosphatase 1 (DUSP1) genes. *J. Biol. Chem.* 285, 2642-2652 (2010).
52. Zhou, J., Huang, K. & Lei, X. G. Selenium and diabetes-evidence from animal studies. *Free Radic. Biol. Med.* 65, 1548-1556 (2013).
53. Dowling, A. L. & Head, E. Antioxidants in the canine model of human aging. *Biochim. Biophys. Acta* 1822, 685-689 (2012).
54. Wong, L. J. et al. Mutations in the MPV17 gene are responsible for rapidly progressive liver failure in infancy. *Hepatology* 46, 1218-1227 (2007).
55. Itoh, S. et al. Novel mechanism for regulation of extracellular SOD transcription and activity by copper: role of antioxidant-1. *Free Radic. Biol. Med.* 46, 95-104 (2009).
56. Machado, V. S. et al. Oxidative stress and inflammatory response biomarkers in dogs with mammary carcinoma. *Path. Res. Practice* 211, 677-681(2015).
57. Woode, R. A. et al. Resveratrol decreases oxidative burst capacity and alters stimulated leukocyte cytokine production in vitro. *Vet. Immunol. Immunopathol.* 163, 164-73 (2015).
58. DeClue, A. E., Sharp, C. R., & Harmon, M. Plasma inflammatory mediator concentrattions at ICU admission in dogs with naturally developed sepsis. *J Vet Med.* 26, 624-630 (2012).
59. Errante, P. R., Frazão, J. B. & Condino-Neto, A. The use of interferon-gamma therapy in chronic granulomatous disease. *Recent Pat. Antiinfect. Drug Discov.* 3, 225-230 (2008).
60. Condino-Neto, A. & Newburger, P. E. Interferon-gamma improves splicing efficiency of CYBB gene transcripts in an interferon-responsive variant of chronic granulomatous disease due to a splice site consensus region mutation. *Blood* 95, 3548-3554 (2000).
61. Bastien, B. C., Patil, A & Satyaraj, E. The impact of weight loss on circulating cytokines in Beagle dogs. *Vet. Immunol. Immunopath.* 163, 174-182 (2015).

62. Sharma, V. & McNeil, J. H. To scale or not to scale: the principles of dose extrapolation. *Br. J. Pharmacol.* 157, 907-921 (2009).
63. Strasser, A. et al. A simple method for the simultaneous separation of peripheral blood mononuclear and polymorphonuclear cells in the dog. *Vet. Immunol. Immunopath.,* 62, 29-35 (1997).
64. Torbergsen, A. C. & Collins, A. R. Recovery of human lymphocytes from oxidative DNA damage; the apperent enhancement of DNA repair by carotenoids. *Eur. J. Nutr.* 39, 80-85 (2000).
65. Jenkinson, A. M., Collins, A. R., Duthie, S. J., Wahle, K. W. & Duthie, G. G. The effect of increased intakes of polyunsaturated fatty acids and vitamin E on DNA damage in human lymphocytes. *FASEB J.* 13, 2138-2142 (1999).
66. Waters, J. D. et al. Noninvasive prediction of prostatic DNA damage by oxidative stress challenge of peripheral blood lymphocytes. *Cancer Epidemiol. Biommarkers Prev.* 16, 1906-1910 (2007).
67. Duthie, S. J. & Dobson, V. L. Dietary flavonoids protect human colonocyte DNA from oxidative attack in vitro. *Eur. J. Nutr.* 38, 28-34 (1999).
68. Singh, N. P., McCoy, M. T., Tice, R. R. & Schneider, E L. A simple technique for quantification of low levels of DNA damage in individual cells. *Exp. Cell Res.* 175, 184-191 (1988).
69. Tice, R. P., Andrews, P. W., Hirai, O. & Singh, N. P. The single cell gel (SCG) assay: an electrophoretic technique for the detection of DNA damage in individual cells. *Adv. Exp. Med. Biol.* 283, 157-164 (1991).
70. Azqueta, A. & Collins, A. R. The essential comet assay: a comprehensive guide to measuring DNA damage and repair. *Arch. Toxicol.* 87, 949-968 (2013).
71. Duthie, S. J., Collins, A. R., Duthie, G. G. & Dobson, V. L. The effect of increased intakes of polyunsaturated fatty acids and vitamin E on DNA damage in human lymphocytes. *Mutat. Res.* 393, 223-231 (1997).
72. Chomczynski, P. & Sacchi, N. Single-step method of RNA isolation by acid guanidinium thiocyanate-phenol-chloroform extraction. *Anal. Biochem.* 162, 156-159 (1987).
73. Livak, K. J. & Schmittgen, T. D. Analysis of relative gene expression data using real-time quantitative PCR and the 2(-Delta Delta C(T)) method. *Methods* 25, 402-408 (2001).
74. Park, E.-J. et al. Induction of retinoid X receptor activity and consequent upregulation of p21$^{WAF1/CIP1}$ by indenoisoquinolines in MCF7 cells. *Cancer Prev. Res.* 4, 1-16 (2011).

Although the foregoing invention has been described in detail for purposes of clarity of understanding, it will be obvious that certain modifications may be practiced within the scope of the appended claims. All publications and patent documents cited herein, as well as text appearing in the figures and sequence listing, are hereby incorporated by reference in their entirety for all purposes to the same extent as if each were so individually denoted.

What is claimed is:

1. A dietary supplement comprising at least three active agents selected from the group consisting of resveratrol, genistein, curcumin, quercetin, and salts thereof, wherein the at least three active agents are in an amount that provides a decrease in plasma level of IL-2 after oral or intravenous administration of the dietary supplement to a mammal for three weeks, wherein the decrease in plasma level of IL-2 is below 0.4 ng/ml, resveratrol comprises from about 1% to about 80% of the dietary supplement by weight, and the dietary supplement, after said administration, provides a serum level of resveratrol of from about 3.86 ng/ml to about 154 µg/ml.

2. The dietary supplement of claim 1, which, after said administration, provides an increase in IL-10 production in the mammal.

3. The dietary supplement of claim 1, which, after said administration, provides an increase in expression of CYBB, DUS, GSR, UCP2, and VIMP genes in the mammal.

4. The dietary supplement of claim 1, which, after said administration, provides a downregulation of ATOX1, CCL5, EPX, MPV17, PRNP and SOD3 gene in the mammal.

5. The dietary supplement of claim 1, which, after said administration, provides:
   (i) a serum level of trans-resveratrol-4'-sulfate of from about 8.9 ng/ml to about 355 µg/ml; (ii) a serum level of trans-resveratrol-3-sulfate of from about 84.9 ng/ml to about 3397 µg/ml; (iii) a serum level of cis-resveratrol-3-sulfate of from about 2.7 ng/ml to about 108 µg/ml; and (iv) a serum level of resveratrol sulfate total of from about 36.7 ng/ml to about 1467 µg/ml.

6. The dietary supplement of claim 1, wherein the dietary supplement comprises resveratrol or a salt thereof, genistein or a salt thereof, curcumin or a salt thereof, and quercetin or a salt thereof;
   resveratrol comprises from about 1% to about 80% of the dietary supplement by weight, genistein comprises from about 0.5% to about 40% of the dietary supplement by weight, curcumin comprises from about 1% to about 80% of the dietary supplement by weight, and quercetin comprises from about 1% to about 80% of the dietary supplement by weight; and
   the dietary supplement provides: (i) a mean serum level of resveratrol of from about 3.86 ng/ml to about 154 µg/ml; (ii) a mean serum level of resveratrol-3-O-glucuronide of from about 12.9 ng/ml to about 514 µg/ml; (iii) a mean serum level of trans-resveratrol-4'-sulfate of from about 8.9 ng/ml to about 355 µg/ml; (iv) a mean serum level of trans-resveratrol-3-sulfate of from about 84.9 ng/ml to about 3397 µg/ml; (v) a mean serum level of cis-resveratrol-3-sulfate of from about 2.7 ng/ml to about 108 µg/ml; (vi) a mean serum level of resveratrol sulfate total of from about 36.7 ng/ml to about 1467 µg/ml; (vii) a mean serum level of genistein-4'-glucuronide of from about 14 µg/ml to about 14167 µg/ml; (viii) a mean serum level of genistein-4'-glucuronide of from about 1.7 µg/ml to about 1700 µg/ml; (ix) a mean serum level of genistein sulfate of from about 54 µg/ml to about 53836 µg/ml; (x) a mean serum level of curcumin glucuronide of from about 6.25 ng/ml to about 250 µg/ml; and (xi) a mean serum level of quercetin of from about 0.2 ng/ml to about 8000 µg/ml, based on oral administration of the dietary supplement to a group of eight mammals.

7. The dietary supplement of claim 1, further comprising flour.

8. The dietary supplement of claim 1, further comprising beef bouillon cubes.

9. The dietary supplement of claim 6, wherein the mammal is a dog.

10. The dietary supplement of claim 1, which is in a form of a tablet.

11. A dietary supplement comprising resveratrol or a salt thereof, genistein or a salt thereof, curcumin or a salt thereof, and quercetin or a salt thereof in an amount that provides (i) an increase in expression of CYBB, DUS, GSR, UCP2, and VIMP genes, (ii) a downregulation of ATOX1, CCL5, EPX, MPV17, PRNP and SOD3 gene, after administration of the dietary supplement to a mammal for three weeks, and (iii) a decrease in plasma level of IL-2, wherein the decrease in plasma level of IL-2 is below 0.4 ng/ml resveratrol comprises from about 1% to about 80% of the dietary supplement by weight, genistein comprises from about 0.5% to about 40% of the dietary supplement by weight, curcumin comprises from about 1% to about 80% of the dietary supplement by weight, and quercetin comprises from about 1% to about 80% of the dietary supplement by weight, and the dietary supplement provides (i) a mean serum level of resveratrol of from about 3.86 ng/ml to about 154 μg/ml; (ii) a mean serum level of resveratrol-3-O-glucuronide of from about 12.9 ng/ml to about 514 μg/ml; (iii) a mean serum level of trans-resveratrol-4'-sulfate of from about 8.9 ng/ml to about 355 μg/ml; (iv) a mean serum level of trans-resveratrol-3-sulfate of from about 84.9 ng/ml to about 3397 μg/ml; (v) a mean serum level of cis-resveratrol-3-sulfate of from about 2.7 ng/ml to about 108 μg/ml; (vi) a mean serum level of resveratrol sulfate total of from about 36.7 ng/ml to about 1467 μg/ml; (vii) a mean serum level of genistein-4'-glucuronide of from about 14 μg/ml to about 14167 μg/ml; (viii) a mean serum level of genistein-4'-glucuronide of from about 1.7 μg/ml to about 1700 μg/ml; (ix) a mean serum level of genistein sulfate of from about 54 μg/ml to about 53836 μg/ml; (x) a mean serum level of curcumin glucuronide of from about 6.25 ng/ml to about 250 μg/ml; and (xi) a mean serum level of quercetin of from about 0.2 ng/ml to about 8000 μg/ml, based on oral administration of the dietary supplement to a group of eight mammals.

12. The dietary supplement of claim 11, wherein the mammal is a dog.

13. The dietary supplement of claim 11, further comprising beef bouillon cubes.

14. The dietary supplement of claim 11, further comprising flour.

15. A dietary supplement comprising resveratrol or a salt thereof, genistein or a salt thereof, curcumin or a salt thereof, and quercetin or a salt thereof in an amount that provides (i) a decrease in plasma level of IL-2, (ii) an increase in plasma level of IFN-γ and (iii) a decrease in plasma level of IL-2, after oral or intravenous administration of the dietary supplement to the mammal for three weeks, wherein the decrease in plasma level of IL-2 is below 0.4 ng/ml, and after said administration, the dietary supplement provides (i) a mean serum level of resveratrol of from about 3.86 ng/ml to about 154 μg/ml; (ii) a mean serum level of resveratrol-3-O-glucuronide of from about 12.9 ng/ml to about 514 μg/ml; (iii) a mean serum level of trans-resveratrol-4'-sulfate of from about 8.9 ng/ml to about 355 μg/ml; (iv) a mean serum level of trans-Resveratrol-3-sulfate of from about 84.9 ng/ml to about 3397 μg/ml; (v) a mean serum level of cis-resveratrol-3-sulfate of from about 2.7 ng/ml to about 108 μg/ml; (vi) a mean serum level of resveratrol sulfate total of from about 36.7 ng/ml to about 1467 μg/ml; (vii) a mean serum level of genistein-4'-glucuronide of from about 14 μg/ml to about 14167 μg/ml; (viii) a mean serum level of genistein-4'-glucuronide of from about 1.7 μg/ml to about 1700 μg/ml; (ix) a mean serum level of genistein sulfate of from about 54 μg/ml to about 53836 μg/ml; (x) a mean serum level of curcumin glucuronide of from about 6.25 ng/ml to about 250 μg/ml; and (xi) a mean serum level of quercetin of from about 0.2 ng/ml to about 8000 μg/ml, based on oral administration of the dietary supplement to a group of eight mammals.

16. The dietary supplement of claim 15, which is a dog biscuit.

* * * * *